(12) United States Patent
Shaw et al.

(10) Patent No.: US 12,098,228 B2
(45) Date of Patent: Sep. 24, 2024

(54) POLYMER LATEX AND ELASTOMERIC FILM MADE THEREFROM HAVING SELF-HEALING PROPERTIES

(71) Applicant: SYNTHOMER (UK) LTD., Harlow (GB)

(72) Inventors: Peter Shaw, Harlow (GB); Amir H. Milani, Manchester (GB); Brian Saunders, Manchester (GB)

(73) Assignee: Synthomer (UK) Limited, Harlow (GB)

( * ) Notice: Subject to any disclaimer, the term of this patent is extended or adjusted under 35 U.S.C. 154(b) by 542 days.

(21) Appl. No.: 17/423,637

(22) PCT Filed: Jan. 21, 2020

(86) PCT No.: PCT/EP2020/051329
§ 371 (c)(1),
(2) Date: Jul. 16, 2021

(87) PCT Pub. No.: WO2020/156868
PCT Pub. Date: Aug. 6, 2020

(65) Prior Publication Data
US 2022/0098346 A1    Mar. 31, 2022

(30) Foreign Application Priority Data
Jan. 28, 2019  (GB) ..................... 1901105

(51) Int. Cl.
| | | |
|---|---|---|
| C08F 236/04 | (2006.01) | |
| C08F 2/30 | (2006.01) | |
| C08F 220/18 | (2006.01) | |
| C08F 220/44 | (2006.01) | |
| C08F 222/10 | (2006.01) | |
| C08F 279/02 | (2006.01) | |
| C08J 5/18 | (2006.01) | |
| C08L 51/04 | (2006.01) | |

(52) U.S. Cl.
CPC .............. *C08F 236/04* (2013.01); *C08F 2/30* (2013.01); *C08F 220/1804* (2020.02); *C08F 220/44* (2013.01); *C08F 222/102* (2020.02); *C08F 279/02* (2013.01); *C08J 5/18* (2013.01); *C08L 51/04* (2013.01); *C08F 2810/20* (2013.01); *C08L 2203/16* (2013.01); *C08L 2207/53* (2013.01)

(58) Field of Classification Search
CPC ........ C08F 236/04; C08F 2/30; C08F 220/18; C08F 220/44; C08F 222/10; C08F 279/02; C08J 5/18; C08L 51/04
USPC ........................................................ 523/201
See application file for complete search history.

(56) References Cited

U.S. PATENT DOCUMENTS

| | | |
|---|---|---|
| 4,244,850 A | 1/1981 | Mylonakis |
| 4,987,184 A | 1/1991 | Wittman et al. |
| 5,306,744 A | 4/1994 | Wolfersberger et al. |
| 11,554,385 B2 | 1/2023 | Lamers et al. |
| 2007/0260015 A1 | 11/2007 | Stork et al. |
| 2009/0176939 A1 | 7/2009 | Ness |
| 2010/0130685 A1 | 5/2010 | Weber et al. |
| 2010/0152365 A1 | 6/2010 | Han et al. |
| 2011/0229646 A1 | 9/2011 | Kim et al. |
| 2016/0272794 A1 | 9/2016 | Han et al. |

FOREIGN PATENT DOCUMENTS

| | | | |
|---|---|---|---|
| CN | 1293032 A | 5/2001 | |
| CN | 102675545 A | 9/2012 | |
| CN | 108350131 A | 7/2018 | |
| EP | 1092421 A2 | 4/2001 | |
| EP | 2465884 A1 * | 6/2012 | ................ C08F 2/22 |
| JP | 6069178 A | 4/1985 | |
| JP | H11503777 A | 3/1999 | |
| JP | H11158223 A | 6/1999 | |
| JP | 2014-500236 A | 1/2014 | |
| WO | 9632429 A1 | 10/1996 | |
| WO | WO-0068304 A1 * | 11/2000 | ............ C08F 285/00 |
| WO | 2012/044929 A2 | 4/2012 | |
| WO | 2017164726 A1 | 9/2017 | |
| WO | 2017209596 A1 | 12/2017 | |
| WO | 2018111087 A1 | 6/2018 | |

OTHER PUBLICATIONS

Kells, A. et al., "Crosslinking in Carboxylated Nitrile Rubber Dipped Films," Jan. 24-25, 2006, Frankfurt, Germany, pp. 1-14, Latex 2006.
International Search Report and Written Opinion for International Application No. PCT/EP2020/051329, dated Apr. 24, 2020, 8 pages.
Office Action (The First Office Action) issued Jun. 28, 2024, by the National Intellectual Property Administration, P. R. China in corresponding Chinese Patent Application No. 202080011019.X and an English translation of the Office Action. (18 pages).

* cited by examiner Deve V Hall

(74) *Attorney, Agent, or Firm* — Buchanan Ingersoll & Rooney PC

(57) ABSTRACT

The present invention relates to an aqueous dispersion comprising core-shell polymer latex particles wherein the shell of the core-shell polymer latex particles bears ethylenically unsaturated groups pending from the polymeric backbone of the shell of the latex particles wherein the ethylenic unsaturation is separated from the polymeric backbone by at least 3 chemical bonds and wherein the shell of the core-shell particles is cross-linked and the core of the core-shell particles is not crosslinked, to a method for making the aqueous dispersion, to an elastomeric film made from the aqueous dispersion, to an article comprising the elastomeric film and to a method for making a self-supported elastomeric film from the aqueous dispersion.

20 Claims, 5 Drawing Sheets

POLYMER LATEX AND ELASTOMERIC FILM MADE THEREFROM HAVING SELF-HEALING PROPERTIES

CROSS-REFERENCE TO RELATED APPLICATIONS

This is the national phase of International Application No. PCT/EP2020/051329, filed 21 Jan. 2020, which claims priority to Great Britain Application No. GB 1901105.5, filed 28 Jan. 2019. The disclosure of each of these applications is incorporated herein by reference in its entirety for all purposes.

FIELD OF INVENTION

The present invention relates in particular but not exclusively to an aqueous dispersion comprising core-shell polymer latex particles that is particularly suitable for the preparation of elastomeric films, to a method for making such an aqueous dispersion, to elastomeric films made from said aqueous dispersions, and to a method for making a self-supported elastomeric film employing said aqueous dispersions.

BACKGROUND OF THE INVENTION

According to the present industry standard, elastomeric films, in particular in dip-molding applications, for example surgical gloves, are made from compounds containing carboxylated acrylonitrile butadiene latices (XNBR). In order to obtain the required mechanical strength for the purpose of use of these elastomeric films, some crosslinking of the films during the manufacturing of the elastomeric films needs to be achieved.

Several different concepts are available in the prior art in order to obtain such crosslinked elastomeric films. One possibility is that the compound for making the elastomeric films contains a conventional sulfur vulcanization system such as sulfur in combination with accelerators, such as thiurams and carbamates and zinc oxide.

Since sulfur vulcanization systems might lead to allergic reactions, alternative concepts to make the latex film curable have been developed. Another possibility is to include in the compound a crosslinker component like, for example polyvalent cation, for example zinc oxide or other poly-functional organic compounds suitable to react with functional groups on the latex particles in order to achieve chemical crosslinking. Furthermore, if the polymer latex bears sufficient amounts of self-crosslinking groups, for example N-methylol amide groups, sulfur vulcanization systems and/or crosslinkers may be totally avoided.

Systems that use specific additives such as sulfur or crosslinkers are summarized in WO 2018/111087 and WO 2017/164726.

WO 2017/209596 discloses a polymer latex for dip-molding applications comprising two different types of latex particles. One kind of latex particle is carboxylated whereas the second kind of latex particle contains oxirane-functional groups.

All these different concepts lead to crosslinked elastomeric films, wherein the crosslinks are in essence irreversible so that that these elastomeric films cannot easily be recycled nor do they show any self-healing properties. For example, if any kind of defect such as pinholes occur during the manufacturing of the elastomeric film because of the lack of self-healing properties of the film, these products need to be scrapped, resulting in non-reusable waste. In addition, if such elastomeric films crack during their use, this cannot be repaired, resulting in an irreversible destruction of the elastomeric film and thus, to failure of the article containing such elastomeric film.

Accordingly, there is a desire in the industry for elastomeric films that have inherent self-healing properties and can potentially be recycled in order to reduce the non-usable waste of such elastomeric films and to avoid final failure of articles comprising such elastomeric films. This would also lead to a more environmentally friendly technology for making elastomeric films. Furthermore, such systems would avoid the need to use materials that could cause so called Type IV allergic reactions.

U.S. Pat. No. 4,244,850, JPS 6069178 and U.S. Pat. No. 5,306,744 disclose polymer latex compositions to be used in coating compositions or in adhesives, comprising polymer latex particles having ethylenically unsaturated groups that may be introduced by reacting functional groups present on the latex particles with ethylenically unsaturated compounds bearing functional groups that are reactive with the functional groups on the latex particles. Although U.S. Pat. No. 5,306,744 and JPS 6069178 disclose core-shell particles obtained by a two-step emulsion polymerization, the core in these particles is crosslinked, wherein the outer shell is not crosslinked. None of these references relate to elastomeric films nor do they address self-healing properties of elastomeric films.

Thus, the present invention seeks to provide a polymer latex composition that is suitable for the preparation of elastomeric films that have self-healing properties.

SUMMARY OF THE INVENTION

According to a first aspect of the invention there is provided an aqueous dispersion comprising core-shell polymer latex particles wherein the shell of the core-shell polymer latex particles bears ethylenically unsaturated groups pending from the polymeric backbone of the shell of the latex particles wherein the ethylenic unsaturation is separated from the polymeric backbone by at least 3 chemical bonds and wherein the shell of the core-shell particles is crosslinked and the core of the core-shell particles is not crosslinked.

Furthermore, according to a further aspect, the present invention also relates to a method for making an aqueous dispersion comprising core-shell polymer latex particles, wherein the shell of the core-shell polymer latex particles bears ethylenically unsaturated groups pending from the polymeric backbone of the shell of the latex particles, wherein the shell of the core-shell particles is crosslinked and the core of the core-shell particles is not crosslinked by aqueous emulsion polymerization comprising at least two steps, wherein I) in a step for making the core of the core-shell particles ethylenically unsaturated monomers comprising no monomers containing more than one non-conjugated ethylenically unsaturated group are polymerized; and II) in a step for making the shell a monomer mixture is polymerized comprising:
  a) monomers selected from conjugated dienes, mono ethylenically unsaturated monomers having no functional groups that can be subsequently reacted after formation of the latex particles to introduce ethylenically unsaturated groups and combinations thereof; and
  b) i) monomers having at least two non-conjugated ethylenically unsaturated groups that exhibit different reactivities in the aqueous emulsion polymerization, wherein at least a portion of the ethylenically unsaturated groups having the lower reactivity remains unreacted after termination of the aqueous emulsion polymerization; and/or ii) mono ethylenically unsaturated monomers having functional groups that can be subsequently reacted after formation of the latex particles to introduce ethylenically unsaturated groups; and c) monomers having at least two non-conjugated ethylenically unsaturated groups different from bi), wherein if no monomers bi) are present at least a portion of said functional groups of the monomers bii) are reacted after termination of the aqueous emulsion polymerization to introduce ethylenically unsaturated groups.

In addition, according to a further aspect the present invention relates to an elastomeric film made from the aqueous dispersion of the present invention, wherein the film is preferably self-supported and substantially free of sulfur crosslinks and substantially free of ionomeric crosslinks.

Another aspect of the present invention relates to a method for making a self-supported elastomeric film comprising:
a) providing a composition comprising the aqueous dispersion as defined above,
b) applying said composition to a substrate to form a wet film,
c) drying and/or curing the wet film to form an elastomeric film, and
d) separating the elastomeric film from the substrate,
e) optionally heat-treating the elastomeric film prior or after step d) at a temperature from 20° C. to 160° C., preferably 250° C. to 100° C., more preferred 75° C. to 100° C.

Furthermore, in a further aspect the present invention also relates to an article comprising the elastomeric film according to the present invention.

In addition, the present Inventors have surprisingly discovered that the elastomeric films obtained from the aqueous dispersion of the present invention in addition to self-healing properties exhibit shape retention properties upon subjecting the elastomeric film to moderate temperatures as will be shown in more detail in the examples.

DETAILED DESCRIPTION OF THE INVENTION

Figure 1:
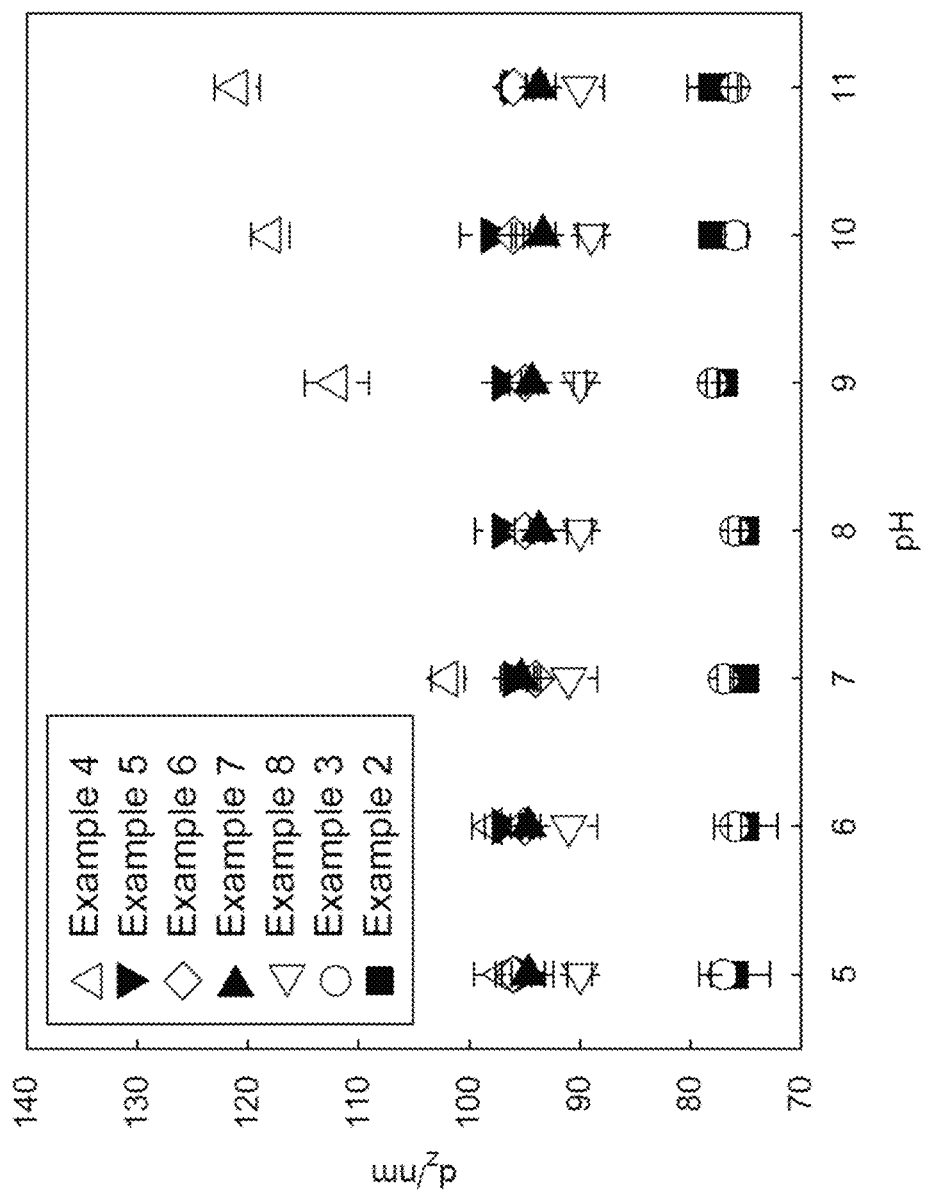
FIG. 1 demonstrates that the presence of a crosslinked shell negated any pH response of the latex.

In the following, the present invention will be illustrated in more detail.

There is shown an aqueous dispersion comprising core-shell latex particles, wherein the shell of the core-shell particles is crosslinked and the core of the core-shell particles is not crosslinked. In particular, the core-shell polymer latex particles bear ethylenically unsaturated groups pending from the polymeric backbone of the shell of the latex particles, wherein the ethylenic unsaturation is separated from the polymeric backbone by at least three chemical bonds.

Thereby, the polymer latex particles are clearly distinguished from core-shell particles wherein a crosslinked shell is formed by polymerization of a monomer mixture containing conjugated diene, like butadiene, since then the remaining double bond resulting from the polymerization of one double bond of the conjugated diene in a free-radical emulsion polymerization process would be separated from the polymeric backbone of the shell by less than three chemical bonds.

In particular, the shell of the core-shell polymer particles may comprise structural units represented by formula (1)

$$-L-CR^1=CR^2R^3 \qquad (1)$$

wherein L is a linear or branched divalent group providing at least two atoms in the chain between —$CR^1=CR^2R^3$ and the polymeric backbone of the shell of the latex particles or a divalent group comprising a cyclic group and $R^1$, $R^2$, and $R^3$ are independently selected from hydrogen and monovalent organic groups, preferably $C_1$-$C_4$-alkyl groups.

In formula (1), -L- may be selected from divalent hydrocarbon groups and groups comprising at least one hetero atom in the chain linking —$CR^1=CR^2R^3$ to the polymeric backbone, preferably -L- comprises a group in the chain linking —$CR^1=CR^2R^3$ to the polymeric backbone selected from ester, ether, urethane, thiourethane, urea, amide groups and combinations thereof.

Thus, there are in principle two different synthetic routes through which the polymer latex particles can be produced. According to one route, the monomer mixture for polymerizing the shell part of the core-shell particles may contain, in addition to monomers having at least two non-conjugated ethylenically unsaturated groups that result in crosslinking of the shell part of the polymer latex particles, monomers having at least two non-conjugated ethylenically unsaturated groups that exhibit different reactivities in aqueous emulsion polymerization, whereby at least a portion of these ethylenically unsaturated groups having the lower activity remains unreacted after termination of the aqueous emulsion polymerization. Thereby, ethylenically unsaturated groups having the required separation from the polymeric backbone of the shell polymer remain present on the surface of the polymer latex particles according to the present invention.

Alternatively, the polymer latex particles may be prepared by polymerizing a monomer mixture for the shell part of the core-shell particles that comprises monoethylenically unsaturated monomers having functional groups that can be subsequently reacted after formation of the latex particles to introduce ethylenically unsaturated groups and then react after termination of the aqueous emulsion polymerization said functional groups to introduce ethylenically unsaturated groups.

Therefore, the core-shell latex particles may be made by aqueous emulsion polymerization comprising at least two steps, wherein
I) in a step for making the core of the core-shell particles ethylenically unsaturated monomers comprising no monomers containing a plurality of one non-conjugated ethylenically unsaturated groups are polymerized; and II) in a step for making the shell a monomer mixture is polymerized comprising:
  a) monomers selected from conjugated dienes, mono ethylenically unsaturated monomers having no functional groups that can be subsequently reacted after formation of the latex particles to introduce ethylenically unsaturated groups and combinations thereof; and
  b) i) monomers having at least two non-conjugated ethylenically unsaturated groups that exhibit different reactivities in the aqueous emulsion polymerization, wherein at least a portion of the ethylenically unsaturated groups having the lower reactivity remains unreacted after termination of the aqueous emulsion polymerization; and/or
    ii) mono ethylenically unsaturated monomers having functional groups that can be subsequently reacted after formation of the latex particles to introduce ethylenically unsaturated groups; and
  c) monomers having at least two non-conjugated ethylenically unsaturated groups different from bi), wherein if no monomers bi) are present at least a portion of said functional groups of the monomers bii) are reacted after termination of the aqueous emulsion polymerization to introduce ethylenically unsaturated groups.

Monomers a)

Monomers a) for the polymerization of the shell part of the core-shell particles of the present invention may suitably be selected from conjugated dienes, aromatic vinyl compounds, linear alkyl esters of ethylenically unsaturated acids, branched alkyl esters of ethylenically unsaturated acids, linear alkyl amides of ethylenically unsaturated acids, branched alkyl amides of ethylenically unsaturated acids, ethylenically unsaturated nitriles, vinyl esters of carboxylic acids, diesters of ethylenically unsaturated acids, vinyl ethers, ethylenically unsaturated silanes, alkenes and any combinations thereof.

Suitable conjugated dienes may be selected from selected from 1,3-butadiene, isoprene, 2,3-dimethyl-1,3-butadiene, 2,3-dimethyl-1,3-butadiene, 2-chloro-1,3-butadiene, 1,3-pentadiene, 1,3-hexadiene, 2,4-hexadiene, 1,3-octadiene, 2-methyl-1,3-pentadiene, 2,3-dimethyl-1,3-pentadiene, 3,4-dimethyl-1,3-hexadiene, 2,3-diethyl-1,3-butadiene, 4,5-diethyl-1,3-octadiene, 3-butyl-1,3-octadiene, 3,7-dimethyl-1,3,6-octatriene, 2-methyl-6-methylene-1,7-octadiene, 7-methyl-3-methylene-1,6-octadiene, 1,3,7-octatriene, 2-ethyl-1, 3-butadiene, 2-amyl-1,3-butadiene, 3, 7-dimethyl-1,3,7-octatriene, 3,7-dimethyl-1,3,6-octatriene, 3,7,11-trimethyl-1,3,6,10-dodecatetraene, 7,11-dimethyl-3-methylene-1,6,10-dodecatriene, 2,6-dimethyl-2,4,6-octatriene, 2-phenyl-1,3-butadiene and 2-methyl-3-isopropyl-1,3-butadiene and 1,3-cyclohexadiene. 1,3-butadiene, isoprene and combinations thereof are the preferred conjugated dienes. 1,3-butadiene is particularly preferred.

Representatives of vinyl-aromatic monomers include, for example, styrene, α-methylstyrene, vinyltoluene, o-methylstyrene, p-methylstyrene, p-tert-butylstyrene, 2,4-dimethylstyrene, 2-methylstyrene, 3-methylstyrene, 4-methylstyrene, 2-ethylstyrene, 3-ethylstyrene, 4-ethylstyrene, 2,4-diisopropylstyrene, 2,4-dimethylstyrene, 4-t-butylstyrene, 5-t-butyl-2-methylstyrene, 2-chlorostyrene, 3-chlorostyrene, 4-chlorostyrene, 4-bromostyrene, 2-methyl-4,6-dichlorostyrene, 2,4-dibromostyrene, vinylnaphthalene, vinyltoluene and vinylxylene, 2-vinylpyridine, 4-vinylpyridine and 1,1-diphenylethylenes and substituted 1,1-diphenylethylenes, 1,2-diphenylethene and substituted 1,2-diphenylethylenes. Mixtures of one or more of the vinyl-aromatic compounds may also be used. The preferred monomers are styrene and α-methylstyrene.

The alkyl esters of ethylenically unsaturated acids may be selected from n-alkyl esters, iso-alkyl esters or tertiary-alkyl esters of (meth)acrylic acid in which the alkyl group has from 1 to 20 carbon atoms, the reaction product of (meth)acrylic acid with glycidyl esters of a neoacid, preferably selected from versatic acid, neodecanoic acid or pivalic acid and alkoxyalkyl (meth)acrylate monomers.

In general, the preferred alkyl esters of (meth)acrylic acids may be selected from C1-C20 alkyl (meth)acrylate, preferably C1-C10-alkyl (meth)acrylates. Examples of such acrylate monomers include n-butyl acrylate, secondary butyl acrylate, methyl acrylate, ethyl acrylate, hexyl acrylate, tert-butyl acrylate, 2-ethyl-hexyl acrylate, isooctyl acrylate, 4-methyl-2-pentyl acrylate, 2-methylbutyl acrylate, methyl methacrylate, butyl methacrylate, n-butyl methacrylate, isobutyl methacrylate, ethyl methacrylate, isopropyl methacrylate, hexyl methacrylate, cyclohexyl methacrylate and cetyl methacrylate. It is particularly preferred to select the esters of (meth)acrylic acids from methyl (meth)acrylate, ethyl (meth)acrylate, propyl (meth)acrylate, butyl (meth)acrylate, 2-ethylhexyl (meth)acrylate and combinations thereof.

Alkoxyalkyl (meth)acrylate monomers which can be used as monomers a) include methoxyethyl methacrylate, ethoxyethyl methacrylate, methoxybutyl methacrylate, ethoxyethyl acrylate, butoxyethyl methacrylate, methoxybutyl acrylate and methoxyethoxyethyl acrylate. Preferred alkoxyalkyl (meth)acrylate monomers are ethoxyethyl acrylate and methoxyethyl acrylate.

The amides of ethylenically unsaturated acids may be selected from (meth)acrylamide, N-methylol (meth)acrylamide and diacetone acrylamide. The preferred amide monomer is (meth)acrylamide.

Examples of ethylenically unsaturated nitrile monomers which can be used for the monomers (a) for the preparation of the shell of the core-shell latex particles according to the present invention include polymerizable unsaturated aliphatic nitrile monomers which contain from 2 to 4 carbon atoms in a linear or branched arrangement, which may be substituted either by acetyl or additional nitrile groups. Such nitrile monomers include acrylonitrile, methacrylonitrile, alpha-cyanoethyl acrylonitrile, fumaronitrile and combinations thereof, with acrylonitrile being most preferred.

Suitable vinyl esters of ethylenically unsaturated acids may be selected from vinyl acetate, vinyl proprionate, vinyl butyrate, vinyl benzoate, vinyl-2-ethylhexanoate, vinyl stearate, and the vinyl esters of versatic acid. The most preferred vinyl ester is vinyl acetate.

Suitable diesters of ethylenically unsaturated acids may be selected from dimethyl maleate, diethyl maleate, dipropyl maleate, dibutyl maleate, dihexyl maleate, di(2-ethylhexyl) maleate, di-n-octyl maleate, di(6-methylheptyl) maleate, dimethyl fumarate, diethyl fumarate, dipropyl fumarate, dibutyl fumarate, dihexyl fumarate, di(2-ethylhexyl) fumarate, di-n-octyl fumarate, di(6-methylheptyl) fumarate. The most preferred diester is dibutyl maleate.

The ethylenically unsaturated silanes may be selected from trialkoxy vinyl esters, for example trimethoxyvinylsilane, triethoxyvinylsilane; trialkoxy (meth)acrylates, for example trimethylsilyl (meth)acrylate and triethylsilyl (meth)acrylate, 3-(trimethoxysilyl)propyl (meth)acrylate and 3-(trimethoxysilyl)propyl (meth)acrylate, 3-methacrylamidopropyl)triethoxysilane, and combinations thereof; and/or the vinyl ethers are selected from alkyl vinyl ethers, for example methyl vinyl ether, ethyl vinyl ether, n-butyl vinyl ether, isobutyl vinyl ether, ethylhexyl vinyl ether, dodecylvinyl ether, octadecyl vinyl ether, and cyclohexyl vinylether.

Monomers bi)

Suitable monomers bi) are selected from allyl (meth)acrylate, allyl crotonate, N,N diallyl (meth)acrylamide, 2-allyloxyethyl (meth)acrylate, 2-allyloxyethoxyethyl (meth)acrylate, vinyloxy-butyl (meth)acrylate and butenyl (meth)acrylate.

Monomers bii)

Suitable monomers bii) for the preparation of the shell of the core-shell particles according to the present invention may be selected from carboxylic acid functional ethylenically unsaturated monomers, oxirane functional ethylenically unsaturated monomers, hydroxyl functional ethylenically unsaturated monomers, isocyanate functional monomers and amino functional ethylenically unsaturated monomers.

The ethylenically unsaturated carboxylic acid monomers suitable as monomers (bii) according to the present invention include monocarboxylic acid and dicarboxylic acid monomers and monoesters of dicarboxylic acid. Carrying out the present invention, it is preferable to use ethylenically unsaturated aliphatic mono- or dicarboxylic acids or anhydrides which contain from 3 to 5 carbon atoms. Examples of monocarboxylic acid monomers include acrylic acid, acrylic anhydride, methacrylic acid, 4-vinylbenzoic acid, trichloroacrylic acid, crotonic acid, 2-carboxyethyl acrylate, monoesters of maleic acid or fumaric acid, for example maleic acid monomethyl ester, maleic acid monoethyl ester, maleic acid monobutyl ester, maleic acid mono hexyl ester, maleic acid mono(2-ethylhexyl) ester, maleic acid monolauryl ester, fumaric acid monomethyl ester, fumaric acid monoethyl ester, fumaric acid monobutyl ester, fumaric acid mono hexyl ester, fumaric acid mono(2-ethylhexyl) ester, fumaric acid monolauryl ester; and examples of dicarboxylic acid monomers include fumaric acid, itaconic acid, 4-methacryloxyethyl trimellitic anhydride, maleic acid and maleic anhydride. Examples of other suitable ethylenically unsaturated acids include vinyl acetic acid, vinyl lactic acid, vinyl sulfonic acid, 2-methyl-2-propene-1-sulfonic acid, styrene sulfonic acid, acrylamidomethyl propane sulfonic acid and the salts thereof. Preferably, the ethylenically unsaturated carboxylic acid monomers are selected from (meth)acrylic acid, crotonic acid, 2-carboxyethyl acrylate, itaconic acid, maleic acid, fumaric acid and combinations thereof.

Suitable oxirane-functional ethylenically unsaturated monomers may be selected from glycidyl (meth)acrylate, allyl glycidylether, vinyl glycidylether, vinyl cyclohexene oxide, limonene oxide, 2-ethylglycidylacrylate, 2-ethylglycidylmethacrylate, 2-(n-propyl)glycidylacrylate, 2-(n-propyl)glycidylmethacrylate, 2-(n-butyl)glycidylacrylate, 2-(n-butyl)glycidylmethacrylate, dimethylglycidyl methacrylate, glycidylmethylmethacrylate, glycidylacrylate, 2,3-epoxybutyl methacrylate, (3',4'-epoxyheptyl)-2-ethylacrylate, (3', 4'-epoxyheptyl)-2-ethylmethacrylate, (6',7'-epoxyheptyl) acrylate, (6',7'-epoxyheptyl)methacrylate, allyl-3,4-epoxyheptylether, 6,7-epoxyheptylallylether, vinyl-3,4-epoxyheptylether, 3,4-epoxyheptylvinylether, 6,7-epoxyheptylvinylether, o-vinylbenzylglycidylether, m-vinylbenzylglycidylether, p-vinylbenzylglycidylether, 3-vinyl cyclohexene oxide, alpha-methyl glycidyl methacrylate, 3,4-epoxycyclohexylmethyl (meth)acrylate, (3-methyloxiran-2-yl) methyl 2-methacrylate, styrene glycidyl ether, 2, 4-vinylphenyl glycidyl ether and combinations thereof. Glycidyl (meth)acrylate is particularly preferred.

The hydroxy alkyl(meth)acrylate monomers include hydroxyalkyl acrylate and methacrylate monomers which are based on ethylene oxide, propylene oxide and higher alkylene oxides or mixtures thereof. Examples are 2-hydroxyethyl acrylate, 3-hydroxypropyl acrylate, 2-hydroxyethyl methacrylate, 2-hydroxypropyl methacrylate and 4-hydroxybutyl acrylate, glycerol monomethacrylate, N-hydroxyethyl acrylamide, N-(2-hydroxypropyl)methacrylamide, 3-Phenoxy 2 hydroxy propyl methacrylate, hydroxypolyethoxy (10) allyl ether, polyethylene glycol- or polypropylene glycol-derived (meth)acrylates for example a polypropylene glycol monomethacrylate containing an average of 6 propylene glycol units. Preferably, the hydroxy alkyl(meth)acrylate monomer is selected from 2-hydroxyethyl (meth)acrylate. Additionally or alternatively, the hydroxy monomers may include phenol (meth)acrylate, dopamine methacrylamide or 4-vinyl phenol.

Examples of isocyanate monomers are 2-(acryloyloxy) ethyl isocyanate and 2-(methacryloyloxy)ethyl isocyanate.

Amino-functional ethylenically unsaturated compounds may be selected from 2-aminoethyl(meth)acrylate, aminopropyl(meth)acrylate and aminobutyl(meth)acrylate, N-(2-aminoethyl) methacrylamide, N-(3-aminopropyl) methacrylamide or salts thereof.

Monomers c)

Suitable monomers c) in order to achieve cross-linking of the shell of the core-shell latex particles of the present invention may be selected from monomers comprising two ethylenically unsaturated groups, preferably selected from divinyl benzene, (meth)acrylates of polyols, allyl ethers of polycarboxylic acids, monomers comprising three ethylenically unsaturated groups, preferably selected from diallyl maleate or trimethylolpropane tri(meth)acrylate, monomers comprising four ethylenically unsaturated groups, preferably selected from pentaerythritol tetra(meth)acrylate and any combinations thereof. Examples of (meth)acrylates of polyols are ethylene glycol di(meth)acrylate, hexanediol di(meth)acrylate, tripropylene glycol di(meth)acrylate, butanediol di(meth)acrylate, neopentyl glycol di(meth)acrylate, diethylene glycol di(meth)acrylate, triethylene glycol di(meth)acrylate, and dipropylene glycol di(meth)acrylate. Further examples of suitable monomers are those cited in EP3119815. The monomers having at least two ethylenically unsaturated groups are preferably selected from divinyl benzene, 1,2 ethyleneglycol di(meth)acrylate, 1,4-butanediol di(meth)acrylate and 1,6-hexanediol di(meth)acrylate.

According to the present invention, it is preferred that the shell of the core-shell particles is prepared by aqueous emulsion polymerization of a mixture of ethylenically unsaturated monomers comprising monomers a), monomers bii) and monomers c) and optionally monomers bi) thereby forming polymer latex particles having a shell bearing a first functional group originating from the functional group of monomers bii); and subsequently reacting said polymer latex particles bearing said first functional group with an ethylenically unsaturated compound having in addition to the ethylenically unsaturation a second functional group that is reactive with the first functional group.

Thus, according to the present invention, monomers bii) may be present and comprise ethylenically unsaturated carboxylic acid, with the result that the first functional group is a carboxyl group and the ethylenically unsaturated compound to be reacted with the polymer latex particles having the second functional group is selected from epoxy-functional ethylenically unsaturated compounds. These epoxy-functional ethylenically unsaturated compounds may be selected from the epoxy compounds as defined above as monomers bii) for the preparation of the shell of the core-shell particles.

Alternatively, the monomers bii) may comprise epoxy-functional ethylenically unsaturated compounds as defined above and the first functional group is an epoxy group and the ethylenically unsaturated compound having the second functional group is selected from ethylenically unsaturated carboxylic acids. These ethylenically unsaturated carboxylic acids might be selected from those carboxylic acid-functional monomers as defined above for use to make the shell of the core-shell particles.

Alternatively, monomers bii) may comprise hydroxy- and/or amino-functional ethylenically unsaturated compounds that may be selected from monomers as defined above, resulting in first functional groups selected from hydroxy and amino groups, and the ethylenically unsaturated compound to be reacted with the polymer latex particles having the second functional group is selected from carboxylic acids, isocyanate- or thioisocyanate-functional ethylenically unsaturated compounds.

Suitable carboxylic acids are listed above; and suitable isocyanate- or thioisocyanate-functional ethylenically unsaturated compounds may be selected from allyl isocyanate, 2-Isocyanatoethyl (meth)acrylate, 3-isopropenyl-α,α'-dimethylbenzyl isocyanate, 2-isocyanatoethyl methacrylate, allyl isothiocyanate, 4-vinylbenzyl isothiocyanate.

According to the present invention, it is preferred that only monomers bii) and no monomers bi) are used for making the shell of the core-shell particles. It is particularly preferred that monomers bii) comprise ethylenically unsaturated carboxylic acids and the ethylenically unsaturated compounds to be reacted with polymer latex particles having the second functional group is selected from epoxy-functional ethylenically unsaturated compounds, preferably as defined above.

The relative amounts of monomers to be used for making the shell of the core-shell particles of the present invention is not particularly critical as long as monomers b) and c) as defined above also with respect to their preferred embodiments are present in sufficient amounts to provide a cross-linked shell and to provide ethylenic unsaturation of the shell, either initially by using the monomers bi) or by subsequent reaction with functional ethylenically unsaturated compounds if monomers bii) are present. Thus, the monomer mixture for making the shell of the core-shell particles of the present invention may comprise 78 to 99.8 wt. % of monomers a); preferably the monomer composition for making the shell of the core-shell particles may comprise 78 to 99 wt. % of monomers a), 0.5 to 16 wt. % of monomers b) and 0.5 to 6 wt. % of monomers c), more preferred 80 to 98 wt. % of monomers a), 1 to 15 wt. % of monomers b) and 0.1 to 5 wt. % of monomers c), even more preferred 85 to 98 wt. % of monomers a), 1 to 10 wt. % of monomers b) and 1 to 5 wt. % of monomers c), even more preferred 88 to 96 wt. % of monomers a), 3 to 8 wt. % of monomers b) and 0.1 to 4 wt. % of monomers c), most preferred 90 to 97 wt. % of monomers a), 2 to 7 wt. % of monomers b), 0.5 to 3 wt. % of monomers c).

Monomers a) that typically constitute the majority of monomers in the monomer mixture for making the shell of the core-shell particles according to the present invention and their relative amounts are selected in order to adjust the desired properties of the polymer latex composition and the elastomeric film prepared therefrom.

Thus, monomers a) may comprise:
15 to 99 wt. % of alkyl(meth)acrylates including alkoxyalky(meth)acrylates
1 to 80 wt. % of ethylenically unsaturated nitrile compounds,
0 to 50 wt. % of vinyl aromatic monomers,
0 to 90 wt. % of conjugated diene,
0 to 18 wt. % of vinyl esters of carboxylic esters and/or vinyl ethers,
0 to 10 wt. % of ethylenically unsaturated compounds bearing silane, and
0 to 18 wt % of ethylenically unsaturated compounds bearing amide groups, whereby the weight percentages are based on the total weight of monomers a).

According to the present invention, the amounts of the above-defined monomers for the monomer mixture a) for the preparation of the shell of the core-shell particles of the present invention may add up to 100 wt. %.

Typically, the amount of alkyl(meth)acrylates including alkoxyalky(meth)acrylates monomer ranges from 15 to 99 wt. %, preferably from 20 to 90 wt. %, more preferred from 40 to 80 wt. %, most preferred from 50 to 75 wt. %, based on the total weight of monomers. Thus, the conjugated diene may be present in amounts of at least 15 wt.-%, at least 20 wt. %, at least 22 wt. %, at least 24 wt. %, at least 26 wt. %, at least 28 wt. %, at least 30 wt. %, at least 32 wt. %, at least 34 wt. %, at least 36 wt. %, at least 38 wt. %, or at least 40 wt. %, based on the total weight of the ethylenically unsaturated monomers (a).

Accordingly, the alkyl(meth)acrylates including alkoxyalky(meth)acrylates monomers can be used in amounts of no more than 95 wt. %, no more than 90 wt. %, no more than 85 wt. %, no more than 80 wt. %, no more than 78 wt. %, no more than 76 wt. %, no more than 74 wt. %, no more than 72 wt. %, no more than 70 wt. %, no more than 68 wt. %, no more than 66 wt. %, no more than 64 wt. %, no more than 62 wt. %, no more than 60 wt. %, no more than 58 wt. %, or no more than 56 wt. %. A person skilled in the art will appreciate that any range between any of the explicitly disclosed lower and upper limit is herein disclosed.

The nitrile monomers can be included in amounts from 1 to 80 wt. %, preferably from 10 to 70 wt. %, or 1 to 60 wt. %, and more preferred from 15 to 50 wt. %, even more preferred from 20 to 50 wt. %, most preferred from 20 to 40 wt. %, based on the total weight of ethylenically unsaturated monomers (a).

Thus, the unsaturated nitrile may be present in amounts of at least 1 wt. %, 5 wt. %, at least 10 wt. %, at least 12 wt. %, at least 14 wt. %, at least 16 wt. %, at least 18 wt. %, at least 20 wt. %, at least 22 wt. %, at least 24 wt. %, at least 26 wt. %, at least 28 wt. %, at least 30 wt. %, at least 32 wt. %, at least 34 wt. %, at least 36 wt. %, at least 38 wt. %, or at least 40 wt. %, based on the total weight of the ethylenically unsaturated monomers (a).

Accordingly, the unsaturated nitrile monomers can be used in amounts of no more than 80 wt. %, no more than 75 wt. %, no more than 73 wt. %, no more than 70 wt. %, no more than 68 wt. %, no more than 66 wt. %, no more than 64 wt. %, no more than 62 wt. %, no more than 60 wt. %, no more than 58 wt. %, no more than 56 wt. %, no more than 54 wt. %, no more than 52 wt. %, no more than 50 wt. %, no more than 48 wt. %, no more than 46 wt. %, or no more than 44 wt. %. A person skilled in the art will appreciate that any range between any of the explicitly disclosed lower and upper limit is herein disclosed.

The vinyl-aromatic compounds can be used in a range of from 0 to 50 wt. %, preferably from 0 to 40 wt. % more preferred from 0 to 25 wt. %, even more preferred from 0 to 15 wt. %, and most preferred from 0 to 10 wt. %, based on the total weight of ethylenically unsaturated monomers (a). Thus, the vinyl-aromatic compound can be present in an amount of no more than 35 wt. %, no more than 30 wt. %, no more than 25 wt. %, no more than 20 wt. %, no more than 18 wt. %, no more than 16 wt. %, no more than 14 wt. %, no more than 12 wt. %, no more than 10 wt. %, no more than 8 wt. %, no more than 6 wt. %, no more than 4 wt. %, no more than 2 wt. %, or no more than 1 wt. %, based on the total weight of ethylenically unsaturated monomers (a). Vinyl-aromatic compounds may also be completely absent.

Typically, the conjugated diene monomers can be present in amount of no more than 90 wt.-%, no more than 85 wt.-%, no more than 80 wt. %, no more than 70 wt. %, no more than 60 wt. %, no more than 50 wt. %, no more than 40 wt. %, no more than 30 wt. %, no more than 20 wt. %, no more than 10 wt. %, no more than 5 wt. %, no more than 2 wt. %, or no more than 1 wt. %, based on the total weight of ethylenically unsaturated monomers (a).

Typically, the vinyl ester and/or vinyl ether monomers can be present in an amount of no more than 18 wt. %, no more than 16 wt. %, no more than 14 wt. %, no more than 12 wt. %, no more than 10 wt. %, no more than 8 wt. %, no more than 6 wt. %, no more than 4 wt. %, no more than 2 wt. %, or no more than 1 wt. %, based on the total weight of ethylenically unsaturated monomers (a).

The ethylenically unsaturated silane compounds can be present in an amount of no more than 10 wt. %, no more than 8 wt. %, no more than 6 wt. %, no more than 4 wt. %, no more than 2 wt. %, or no more than 1 wt. %, based on the total weight of ethylenically unsaturated monomers (a). In particular, the ethylenically unsaturated silane compounds may be present in an amount of 0.05 to 5.0 wt. %, preferably 0.3 to 2.0 wt. %, more preferred 0.3 to 1.0 wt. %, based on the total weight of ethylenically unsaturated monomers (a).

Typically, amides of ethylenically unsaturated acid can be present in an amount of no more than 18 wt. %, no more than 16 wt. %, no more than 14 wt. %, no more than 12 wt. %, no more than 10 wt. %, no more than 8 wt. %, no more than 6 wt. %, no more than 4 wt. %, no more than 2 wt. %, or no more than 1 wt. %, based on the total weight of ethylenically unsaturated monomers (a).

Furthermore, monomers c) having at least two non-conjugated ethylenically unsaturated groups can be present in the monomer mixture for the preparation of the shell of the core-shell polymer latex particles of the present invention in an amount 0.1 to 6.0 wt. %, preferably 0.1 to 3.5 wt. %, based on the total weight of ethylenically unsaturated monomers. Typically, these monomers can be present in an amount of no more than 6 wt. %, no more than 4 wt. %, no more than 2 wt. %, no more than 1 wt. %, based on the total weight of ethylenically unsaturated monomers. in the monomer mixture for the preparation of the shell of the core-shell polymer latex particles of the present invention In the monomer mixture for the preparation of the shell of the core-shell particles of the present invention, monomers b) are typically present in an amount of 0.1 to 16 wt. %, based on the total weight of monomers in the mixtures. Monomers bi) may be present in an amount of up to 15 wt. %, up to 14 wt. %, up to 13, wt. %, up to 12 wt. %, up to 11 wt. %, up to 10 wt. %, up to 9 wt. %, up to 8 wt. %, up to 7 wt. %, up to 6 wt. %, up to 5 wt. %, up to 4 wt. %, up to 3 wt. %, up to 2 wt. %, up to 1 wt. %. As mentioned above, preferably no monomers bi) are present in the monomer mixture for preparing the shell of the core-shell particles according to the present invention.

In case the monomer bii) is selected from ethylenically unsaturated carboxylic acids and oxirane-functional ethylenically unsaturated compounds, preferably as defined above, these compounds are present in amounts from 0.05 to 10 wt. %, particularly from 0.1 to 10 wt. % or 0.05 to 7 wt. %, preferably from 0.1 to 9 wt. %, more preferred from 0.1 to 8 wt. %, even more preferred from 1 to 7 wt. %, most preferred from 2 to 7 wt. %, based on the total weight of the monomer for the preparation of the shell of the core-shell particles. Thus, the ethylenically unsaturated carboxylic acid monomer or the oxirane-functional ethylenically unsaturated monomers may be present in amounts of at least 0.01 wt. %, at least 0.05 wt. %, at least 0.1 wt. %, at least 0.3 wt. %, at least 0.5 wt. %, at least 0.7 wt. %, at least 0.9 wt. %, at least 1 wt. %, at least 1.2 wt. %, at least 1.4 wt. %, at least 1.6 wt. %, at least 1.8 wt. %, at least 2 wt. %, at least 2.5 wt. %, or at least 3 wt. %. Likewise, the ethylenically unsaturated acid monomers or the oxirane-functional ethylenically unsaturated monomers may be present in amounts of no more than 10 wt. %, no more than 9.5 wt. %, no more than 9 wt. %, no more than 8.5 wt. %, no more than 8 wt. %, no more than 7.5 wt. %, no more than 7 wt. %, no more than 6.5 wt. %, no more than 6 wt. %, no more than 5.5 wt. %, or no more than 5 wt. %, based on the total weight of ethylenically unsaturated monomers for the preparation of the shell of the core-shell particles according to the present invention. A person skilled in the art will appreciate that any range defined by an explicitly disclosed lower limit and an explicitly disclosed upper limit is disclosed herewith.

In case the monomers bii) are selected from hydroxyl-functional and/or amino-functional ethylenically unsaturated monomers, these monomers may be present in amounts from 0.05 to 18 wt. %, particularly from 0.1 to 15 wt. % or 0.05 to 10 wt. %, preferably from 0.1 to 12 wt. %, more preferred from 1 to 10 wt. %, even more preferred from 2 to 8 wt. %. Thus, the hydroxy- and or amino-functional ethylenically unsaturated monomers may be present in amounts of at least 0.01 wt. %, at least 0.05 wt. %, at least 0.1 wt. %, at least 0.3 wt. %, at least 0.5 wt. %, at least 0.7 wt. %, at least 0.9 wt. %, at least 1 wt. %, at least 1.2 wt. %, at least 1.4 wt. %, at least 1.6 wt. %, at least 1.8 wt. %, at least 2 wt. %, at least 2.5 wt. %, or at least 3 wt. %. Likewise, the hydroxy-functional and/or amino-functional ethylenically unsaturated monomers may be present in an amount of no more than 18 wt. %, no more than 16 wt. %, no more than 15 wt. %, no more than 14 wt. %, no more than 13 wt. %, no more than 12 wt. %, no more than 11 wt. %, no more than 10 wt. %, no more than 9.5 wt. %, no more than 9 wt. %, no more than 8.5 wt. %, no more than 8 wt. %, no more than 7.5 wt. %, no more than 7 wt. %, no more than 6.5 wt. %, no more than 6 wt. %, no more than 5.5 wt. %, or no more than 5 wt. %, based on the total weight of ethylenically unsaturated monomers for making the shell for the core-shell particles according to the present invention. A person skilled in the art will appreciate that any range defined by an explicitly disclosed lower limit and an explicitly disclosed upper limit is disclosed herewith.

The monomer composition for making the core of the core-shell particles according to the present invention is not particularly limited as long as the monomers are selected such that no internal crosslinking of the core takes place. Thus, the monomer mixture for making the core does not contain monomers having a plurality of non-conjugated ethylenically unsaturated groups in the molecule. Conjugated dienes may be present, but then preferably the polymerization conditions are selected to avoid gelling of the core part, preferably by using molecular weight regulators for example alkyl mercaptan during the emulsion polymerization process.

In particular, the monomers for the preparation of the core of the core-shell particles according to the present invention may be selected from the monomers a) as described above for the monomer mixture for making the shell of the core-shell particles according to the present invention. It is preferred that the monomer mixture for making the core contains 50 to 100 wt. % of alkyl(meth)acrylate monomers, based on the total weight of monomers for making the core of the core-shell particles according to the present invention. Preferably, the alkyl group contains 1 to 20 carbon atoms, more preferred 2 to 12 carbon atoms, even more preferred 3 to 10 carbon atoms, and most preferred 4 to 8 carbon atoms. Thus, alkyl(meth)acrylate monomers may be present in the mixture for polymerizing the core of the core-shell particles according to the present invention in amounts of at least 55 wt. %, at least 60 wt. %, at least 65 wt. %, at least 70 wt. %, at least 75 wt. %, at least 80 wt. %, at least 82 wt. %, at least 85 wt. %, at least 87 wt. %, at least 90 wt. %, based on the total weight of monomers for making the core of the core-shell particles according to the present invention. The remaining monomers may be particularly selected from conjugated dienes, vinyl aromatic monomers, ethylenically unsaturated amides, ethylenically unsaturated nitrile, alkoxy alkyl(meth)acrylate, vinyl esters and vinyl ethers as defined above for the monomers a) for making the shell of the core-shell particles of the present invention.

In particular, conjugated dienes may be present in amounts of no more than 90 wt. %, no more than 80 wt. %, no more than 70 wt. %, no more than 60 wt. %, no more than 50 wt. %, no more than 40 wt. %, no more than 30 wt. %, no more than 20 wt. %, no more than 10 wt. %, no more than 2 wt. %, based on the total weight of monomers for making the core of the core-shell particles according to the present invention. In particular, conjugated dienes may be absent.

In particular, vinyl aromatic compounds may be present in amounts of no more than 20 wt. %, no more than 18 wt. %, no more than 16 wt. %, no more than 14 wt. %, no more than 12 wt. %, no more than 10 wt. %, no more than 8 wt. %, no more than 6 wt. %, no more than 4 wt. %, no more than 2 wt. %, based on the total weight of monomers for making the core of the core-shell particles according to the present invention. In particular, vinyl aromatic compounds may be absent.

In particular, ethylenically unsaturated amides may be present in amounts of no more than 20 wt. %, no more than 18 wt. %, no more than 16 wt. %, no more than 14 wt. %, no more than 12 wt. %, no more than 10 wt. %, no more than 8 wt. %, no more than 6 wt. %, no more than 4 wt. %, no more than 2 wt. %, based on the total weight of monomers for making the core of the core-shell particles according to the present invention. In particular, ethylenically unsaturated amides may be absent.

In particular, vinyl esters or ethers may be present in amounts of no more than 20 wt. %, no more than 18 wt. %, no more than 16 wt. %, no more than 14 wt. %, no more than 12 wt. %, no more than 10 wt. %, no more than 8 wt. %, no more than 6 wt. %, no more than 4 wt. %, no more than 2 wt. %, based on the total weight of monomers for making the core of the core-shell particles according to the present invention. In particular, vinyl esters or ethers may be absent.

In particular, alkoxyalkyl(meth)acrylates may be present in amounts of no more than 20 wt. %, no more than 18 wt. %, no more than 16 wt. %, no more than 14 wt. %, no more than 12 wt. %, no more than 10 wt. %, no more than 8 wt. %, no more than 6 wt. %, no more than 4 wt. %, no more than 2 wt. %, based on the total weight of monomers for making the core of the core-shell particles according to the present invention. In particular, alkoxyalkyl(meth)acrylates may be absent.

In addition, the monomer mixture for making the core of the core-shell particles according to the present invention may contain minor amounts of ethylenically unsaturated acids, suitably selected from the ethylenically unsaturated acids as described above for the monomer mixture for making the shell of the core-shell particles. Thus, such ethylenically unsaturated carboxylic acid may be present in amounts of up to 20 wt. %, up to 16 wt. %, up to 12 wt. %, up to 8 wt. %, up to 6 wt. %, up to 4 wt. %, up to 3 wt. %, up to 2 wt. %, up to 1 wt. %, based on the total weight of monomers for making the core of the core-shell particles according to the present invention. Ethylenically unsaturated acids may also be completely absent.

The core of the core-shell particles according to the present invention may also be formed from a separately produced seed latex as long as the above requirements defined for the core are fulfilled for the seed latex. Alternatively, such a seed latex might also be produced in situ at the beginning of the emulsion polymerization prior to the polymerization of the core monomers. Alternatively, such a seed latex might also be produced in situ at the beginning of the emulsion polymerization prior to the polymerization of the shell monomers.

It is also possible that the core-shell polymerization according to the present invention is performed as a seeded core-shell polymerization, whereby then the seed latex might either be pre-formed or formed in situ at the beginning of the core-shell emulsion polymerization.

In the core-shell particles of the present invention, the shell may constitute 10 to 90 wt.-%, preferably 20 to 80 wt.-%, more preferred 20 to 50 wt. %, most preferred 25 to 45 wt.-% and the core may constitute 90 to 10 wt.-%, preferably 80 to 20 wt. %, more preferred 80 to 50 wt.-%, most preferred 75 to 55 wt.-% of the total weight of the core-shell particles. In case the core is formed by a pre-formed seed or in situ seed or the core-shell polymerization is conducted in presence of a pre-formed or in situ seed, the seed, when defining the relative amounts of core and shell of the core-shell particles according to the present invention is calculated as part of the core of the core-shell particles. The seed my constitute 0 to 100 wt.-%, preferably 5 to 30 wt.-%, more preferred 10 to 30 wt.-%, even more preferred 15 to 30 wt.-% and most preferred 20 to 30 wt.-% of the total weight of the core.

The monomers for making the core and for making the shell may be selected so that the core has a lower glass transition temperature $T_g$ than the shell, wherein preferably the $T_g$ of the core is below 0° C., preferably below −20° C., and the $T_g$ of the shell is above 0° C., preferably above 20° C., as measured by dynamic mechanical thermal analysis at a fixed frequency of 1 Hz and a heating rate of 3° C. per minute.

In case the monomers for making the shell of the core-shell particles according to the present invention comprise monomers bii), the core-shell particles according to the present invention after termination of the emulsion polymerization are reacted with ethylenically unsaturated compounds bearing a second functionality which is reactive with the first functionality of monomers bii), building part of the shell of the core-shell particles of the present invention.

The amount of the ethylenically unsaturated compound bearing the second functionality is selected to constitute at least 20 mol %, based on total moles of first functionalities introduced into the core-shell particles according to the present invention of the core-shell particles that are reacted with the ethylenically unsaturated compound bearing the second functionality. Preferably, the amount is selected to constitute at least 25 mol %, at least 30 mol %, at least 35 mol %, at least 40 mol %, at least 42 mol %, at least 45 mol %, at least 47 mol %, at least 50 mol %, at least 52 mol %, at least 55 mol %, at least 57 mol %, or at least 60 mol % based on the total moles of first functional groups in the shell of the core-shell particles reacted with the ethylenically unsaturated compound bearing the second functionality. Likewise, the ethylenically unsaturated compound bearing the second functionality is reacted in amounts constituting no more than 100 mol %, no more than 90 mol %, no more than 85 mol %, no more than 80 mol %, no more than 77 mol %, no more than 75 mol %, no more than 72 mol %, no more than 70 mol %, no more than 68 mol %, no more than 65 mol %, no more than 62 mol % of the total moles of the first functionality present in the shell of the core-shell particles reactive with the ethylenically unsaturated compound bearing the second functionality. A person skilled in the art will appreciate that all ranges defined by any of the lower or upper limits as defined above are herewith disclosed.

Surprisingly it has been found that it is possible to produce the self-supporting elastomeric films by modifying the core-shell latex of this invention by subsequent reaction with a difunctional monomer, one functionality therein being capable of reacting with suitably reactive groups on the core-shell latex of this invention, and the other capable of reacting, for example by polymerization, in the presence of oxygen, or a free radical initiator, or a suitable controlled radical initiator system known in the state of the art for example RAFT, ATRP, MADIX or NMP. Such a reaction can be exemplified by the choice of a core-shell latex of this invention which possesses carboxylic acid functionality; preferably, but not necessarily exclusively, this functionality is located at the surface of the latex particles, and it can be reacted with a suitable monomer for example glycidyl methacrylate. Furthermore, it was found that this esterification reaction could be carried out either at a pH above 8, or preferably at a pH below 8, preferably at pH 7 or less, more preferred at pH 6 or less, most preferred at a pH of 5 or less. Furthermore, this esterification reaction may, or may not be carried out in the presence of catalysts known in the state of the art, for example metal ions, preferably multivalent metal ions, for example zinc acetate can be used; or quaternary phosphonium or ammonium slats may be employed, especially useful is cetyl dimethyl benzyl ammonium chloride, tetrabutyl ammonium hydroxide or tetramethylguanidine. Furthermore, the difunctional monomer may, or may not react with another monomer in the core-shell latex of this invention.

The quantity of monomer to be added to functionalize the core-shell latex may be lower than the stoichiometric amount required to react with all of the available groups of the core-shell latex, alternatively the quantity of monomer to be added to functionalize the core-latex may be greater than the stoichiometric amount required to react with all of the available groups of the core-shell latex. Preferably an excess of the functional monomer is employed, this excess may be up to 2 times, up to 3 times or no more than 4 times the available groups. If an excess of the functional monomer is present, then efforts should be made to minimize this excess of unreacted monomer in the final latex. This can be achieved through washing the latex with a solvent in which the functionalized monomer is soluble, but which the latex particle is not soluble, such a solvent is chloroform. Alternatively, the unreacted difunctional monomer may remain in the latex.

The core-shell particles according to the present invention can be made by standard seeded or non-seeded core-shell emulsion polymerization processes. Particularly suitable for making the seed is the process as described in WO2017164726 (A1).

The emulsion (or latex) polymerization may be carried out under an inert atmosphere for example that provided by nitrogen or argon, or it may not be carried out under an inert atmosphere. To a dispersion of the seed particles is added a delayed monomer charge defining the core as described above (typically comprising a chain transfer agent), and following completion of this monomer feed and a post-cooking period, the monomer mixture defining the shell as described above is then added using a continuous monomer addition, also known as a delayed addition approach. Alternatively, the shell may be created by the addition of a single aliquot of the desired monomer mixture, or a number of aliquots of the desired monomer mixture. Preferably the components comprising the delayed monomer mixture are not varied during the addition.

The core does not comprise a crosslinked structure. The shell may or may not form a continuous layer around the core, preferably the shell forms a continuous layer around the core. The shell comprises a crosslinked structure. Alternatively, the emulsion (or latex) polymerization may be carried out with the formation of an in situ seed typically created by the addition of an aliquot of the core monomers, which is allowed to polymerize, and the delayed monomers are then added upon detection of this polymerization exotherm. The preferred option is to carry out the core-shell latex polymerization in a single vessel, in a sequential manner.

The process for the preparation of the above-described polymer latex can be performed at temperatures of from 0 to 130° C., preferably of from 0 to 100° C., particularly preferably of from 5 to 70° C., very particularly preferably of from 5 to 60° C., in the presence of no or one or more emulsifiers, no or one or more colloids and one or more initiators. The temperature includes all values and sub-values therebetween, especially including 5, 10, 15, 20, 25, 30, 35, 40, 45, 50, 55, 60, 65, 70, 75, 80, 85, 90, 95, 100, 105, 110, 115, 120 and 125° C.

Initiators which can be used when carrying out the present invention include water-soluble and/or oil-soluble initiators which are effective for the purposes of the polymerization. Representative initiators are well known in the technical area and include, for example: azo compounds (for example, AIBN, AMBN and cyanovaleric acid) and inorganic peroxy compounds, for example hydrogen peroxide, sodium, potassium and ammonium peroxydisulfate, peroxycarbonates and peroxyborates, as well as organic peroxy compounds, for example alkyl hydroperoxides, dialkyl peroxides, acyl hydroperoxides, and diacyl peroxides, as well as esters, for example tertiary butyl perbenzoate and combinations of inorganic and organic initiators.

The initiator is used in a sufficient amount to initiate the polymerization reaction at a desired rate. In general, an amount of initiator of from 0.01 to 5, preferably of from 0.1 to 4%, by weight, based on the weight of the total polymer, is sufficient. The amount of initiator is most preferably of from 0.01 to 2% by weight, based on the total weight of the polymer. The amount of initiator includes all values and sub-values therebetween, especially including 0.01, 0.1, 0.5, 1, 1.5, 2, 2.5, 3, 4 and 4.5% by weight, based on the total weight of the polymer.

The above-mentioned inorganic and organic peroxy compounds may also be used alone or in combination with one or more suitable reducing agents, as is well known in the art. Examples of such reducing agents which may be mentioned are sulfur dioxide, alkali metal disulfites, alkali metal and ammonium hydrogen sulfites, thiosulfates, dithionites and formaldehyde sulfoxylates, as well as hydroxylamine hydrochloride, hydrazine sulfate, iron (II) sulfate, cuprous naphthanate, glucose, sulfonic acid compounds for example sodium methane sulfonate, amine compounds for example dimethylaniline and ascorbic acid. The quantity of the reducing agent is preferably 0.03 to 10 parts by weight per part by weight of the polymerization initiator.

The initiator is present during the polymerization of the initial monomer charge used to form the seed, be it an external seed or an in-situ seed, the latter approach is preferred because it was found that that this does not require additional initiator to be added to the core-shell latex polymerization reaction. Alternatively, additional aliquots of initiator may be added during the polymerization process, or after completion of the delayed monomers to reduce the final level of free monomers in the core-shell latex.

Surfactants or emulsifiers which are suitable for stabilizing the latex particles include those conventional surface-active agents for polymerization processes. The surfactant or surfactants can be added to the aqueous phase and/or the monomer phase. An effective amount of surfactant in a seed process is the amount which was chosen for supporting the stabilization of the particle as a colloid, the minimization of contact between the particles and the prevention of coagulation. In a non-seeded process, an effective amount of surfactant is the amount which was chosen for influencing the particle size.

The effective amount of surfactant is the amount which was chosen for either process which created a suitable particle size for the seed latex, be it external or in-situ, furthermore a portion of the surfactant was also required to produce the pre-emulsion for both the monomer(s) being used to generate the core, and/or the monomers being used to create the shell, the total amount of surfactant being such that it maintained a stable latex during the creation of both the core and the shell, and additionally during the functionalization of the latex, and which minimized the nucleation of any new particles.

Representative surfactants include saturated and ethylenically unsaturated sulfonic acids or salts thereof, including, for example, unsaturated hydrocarbonsulfonic acid, for example vinylsulfonic acid, allylsulfonic acid and methallylsulfonic acid, and salts thereof; aromatic hydrocarbon acids, for example, p-styrenesulfonic acid, isopropylbenzenesulfonic acid and vinyloxybenzenesulfonic acid and salts thereof; sulfoalkyl esters of acrylic acid and methacrylic acid, for example, sulfoethyl methacrylate and sulfopropyl methacrylate and salts thereof, and 2-acrylamido-2-methylpropanesulfonic acid and salts thereof; alkylated diphenyl oxide disulfonates, sodium dodecylbenzenesulfonates and dihexyl esters of sodium sulfosuccinate, Sodium alkyl esters of sulfonic acid, sodium alkylethoxy esters of sulfonic acid, ethoxylated alkylphenols and ethoxylated alcohols; fatty alcohol (poly)ethersulfates.

The type and the amount of the surfactant is governed typically by the number of particles, their size and their composition. Typically, the surfactant is used in amounts of from 0 to 20, preferably from 0 to 10, more preferably from 0 to 5, wt. %, based on the total weight of the monomers. The amount of surfactant includes all values and sub-values there between, especially including 0, 0.1, 0.5, 1, 2, 3, 4, 5, 6, 7, 8, 9, 10, 11, 12, 13, 14, 15, 16, 17, 18 and 19 wt. %, based on the total weight of the monomer. According to one embodiment of the present invention, the polymerization is conducted without using surfactants.

Various protective colloids can also be used instead of or in addition to the surfactants described above. Suitable colloids include polyhydroxy compounds, for example partially acetylated polyvinyl alcohol, casein, hydroxyethyl starch, carboxymethylcellulose, hydroxyethylcellulose, hydroxypropylcellulose, polysaccharides, and degraded polysaccharides, polyethylene glycol and gum arabic. The preferred protective colloids are carboxymethylcellulose, hydroxyethylcellulose and hydroxypropylcellulose. In general, these protective colloids are used in contents of from 0 to 10, preferably from 0 to 5, more preferably from 0 to 2 parts by weight, based on the total weight of the monomers. The amount of protective colloids includes all values and sub-values therebetween, especially including 1, 2, 3, 4, 5, 6, 7, 8 and 9 wt. %, based on the total weight of the monomers.

In case the polymer latex composition is used in dip-molding applications, it is preferred that the polymer latex composition has a certain maximum electrolyte stability determined as critical coagulation concentration of less than 30 mmol/l calcium chloride, preferably less than 25 mmol/l, more preferred less than 20 mmol/l, most preferred less than 10 mmol/l (determined for a total solids content of the composition of 0.1% at pH 10 and 23° C.).

It is frequently advisable to perform the emulsion polymerization additionally in the presence of buffer substances and chelating agents. Suitable substances are, for example, alkali metal phosphates and pyrophosphates (buffer substances) and the alkali metal salts of ethylenediaminetetraacetic acid (EDTA) or hydroxyl-2-ethylenediaminetriacetic acid (HEEDTA) as chelating agents. The quantity of buffer substances and chelating agents is usually 0.001-1.0 wt. %, based on the total quantity of monomers.

In the Examples of this invention, it was found that the presence of a buffer was not necessary to create a stable latex, and so typically the final pH of the core-shell latex was less than 5, typically it was approximately 3.

Furthermore, it may be advantageous to use chain transfer agents (regulators) in emulsion polymerization. Typical agents are, for example, organic sulfur compounds, for example thioesters, 2-mercaptoethanol, 3-mercaptopropionic acid and C1-C12 alkyl mercaptans, n dodecylmercaptan and t-dodecylmercaptan being preferred. The quantity of chain transfer agents, if present, is usually 0.05-3.0 wt. %, preferably 0.2-2.0 wt. %, based on the total weight of the used monomers.

Furthermore, it can be beneficial to introduce partial neutralization to the polymerization process. A person skilled in the art will appreciate that by appropriate selections of this parameter the necessary control can be achieved.

Various other additives and ingredients can be added in order to prepare the latex composition of the present invention. Such additives include, for example: antifoams, wetting agents, thickeners, plasticizers, fillers, pigments, dispersants, optical brighteners, crosslinking agents, accelerators, antioxidants, biocides and metal chelating agents. Known antifoams include silicone oils and acetylene glycols. Customary known wetting agents include alkylphenol ethoxylates, alkali metal dialkylsulfosuccinates, acetylene glycols and alkali metal alkylsulfate. Typical thickeners include polyacrylates, polyacrylamides, xanthan gums, modified celluloses or particulate thickeners, for example silicas and clays. Typical plasticizers include mineral oil, liquid polybutenes, liquid polyacrylates and lanolin. Zinc oxide is a suitable ionic crosslinking agent. Titanium dioxide ($TiO_2$), calcium carbonate and clay are the fillers typically used. Known accelerators and secondary accelerators include dithiocarbamates like zinc diethyl dithiocarbamate, zincdibutyl dithiocarbamate, zinc dibenyl dithiocarbamate, zinc pentamethylene dithiocarbamate (ZPD), xanthates, thiurams like tetramethylthiuram monosulfide (TMTM), Tetramethylthiuram disulfide (TMTD), tetraethylthiuram disulfide (TETD), dipentamethylenethiuram hexasulfide (DPTT), and amines, for example diphenylguanidine (DPG), di-o-tolylguanidine (DOTG), o-tolylbiguanidine (OTBG).

As mentioned above, the present invention also relates to an elastomeric film made from the aqueous dispersion according to the present invention.

One advantage of the present invention is that the core-shell polymer latex particles according to the present invention allows for the preparation of elastomeric films without the use of conventional sulfur vulcanization in that elemental sulfur and suitable accelerators are added to a compound comprising the polymer latex particles. It is also not necessary that multivalent cations like zinc compounds are added to the compounded latex for making the elastomeric film.

Thus, in a process for making a self-supported elastomeric film, as defined above in the summary of the invention, it is preferred that the providing step a) neither includes the addition of elemental sulfur and accelerators for sulfur vulcanization nor the addition of zinc compounds to the composition; thereby, preferably the composition in step a) has a pH of at most 8.5, preferably of at most 8.0, preferably of at most 7.5, more preferably of at most 7.

The elastomeric film may be obtained by casting, dip-molding, spraying or knife coating.

The elastomeric film, prior or after the separation of the elastomeric film from the substrate, may be heat-treated at a temperature of from 40° C. to 180° C., preferably 60° C. to 100° C., more preferred 75° C. to 100° C. Thus, according to the present invention, the elastomeric film is preferably self-supported and substantially free of sulfur crosslinks and substantially free of ionomeric crosslinks.

Furthermore, the present invention also relates to an article comprising the above-defined elastomeric film. According to the present invention, the elastomeric film may have a first and second outer surface and an inner core between the first and second outer surface, wherein there is a higher degree of crosslinking between polymeric particles at the first and second outer surface than in the inner core of the film.

The article according to the present invention may be selected from disposable gloves including surgical gloves and examination gloves, industrial gloves, household gloves, fabric supported gloves, medical devices for example catheters, condoms and femidoms or the article includes binder ingredients for an energy cell that preferably is a battery containing lithium ions.

The present invention will now be further illustrated with reference to the following examples.

EXAMPLES

Determination of Physical Parameters:

The latexes (also known as emulsions or dispersions) were characterized by determination of total solids content (TSC), pH value and z-average particle size. Furthermore, the final films were tested for tensile properties both before and after being cut and re-rejoined. Wherein a film which was cut into 2 halves and subsequently the 2 halves were then held together was capable of demonstrating a tensile strength when the thus joined 2 halves were subsequently separated, was said to be self-healing.

Determination of Total Solid Contents (TSC):

The TSC of the dispersion samples was measured gravimetrically. The latex was gently stirred by manually swirling the contents. Three aliquots of the latex (~2.0 g) were pipetted into pre-weighed aluminum dishes and weighed before drying in a preheated oven set at 80° C. for 24 h. After cooling to room temperature the final weight was then determined. The TSC is calculated as follows:

$$TSC\ (\%) = (m_o/m_i) \times 100 \tag{1}$$

whereby $m_o$ and $m_i$ are the weight of the dried sample, and weight of the latex sample respectively. The average value of three samples tested was used.

Determination of pH Value:

A CyberScan model of pH meter was used to measure the pH of the dispersions)

Determination of Particle Size (PS):

Dynamic Light Scattering

Dynamic light scattering (DLS) was conducted using a Malvern Zetasizer Nano ZS90 (Malvern Instruments Ltd.), fitted with a 20 mW He—Ne laser. Typically, the sample had a final concentration of 0.01 wt. % to ensure that the photon count rate remained between 100 and 200 kcps (kilocounts per second). The measurement was performed at 25° C. The value was recorded as the z-average particle size (di).

Transmission Electron Microscopy

Transmission electron microscopy was performed using a Philips CM200 instrument operating at 200 kV. For a typical preparation, 0.4 mL of 0.2 wt. % of latex was mixed with 1.6 mL of 2 wt. % of phosphotungstic acid ($H_3O_{40}PW_{12}$) for at least 15-20 minutes at room temperature. The phosphotungstic acid was used as a negative staining agent for the particle specimen. The final mixture concentrations used were approximately 0.04 wt. %. A single drop (μL) of the mixture was pipetted onto a 300-mesh copper of holey carbon grid (Agar Scientific Ltd.) and left for 2 minutes before the excess liquid was drained (using tissue to absorb the excess). The samples were left to dry overnight in a desiccator. At least 100 particles were analysed to calculate the number-average diameter ($d_{TEM}$) by using the following equation:

$$d_{TEM} = \Sigma n_i d_i / \Sigma n_i \tag{2}$$

whereby $d_i$ is diameter of particles in group i, and $n_i$ is the number of particles in group i. The coefficient of variation (CV) was calculated from the standard deviation (SD) using Equation (3):

$$CV = (100 \times SD)/d_{TEM} \tag{3}$$

In the following Examples, the CV is given in parenthesis after the average particle size number.

Potentiometric Titration of Latex Samples

A Mettler Toledo DL15 Titrator was used to determine the carboxylic acid contents of the sample. For a typical preparation, 1 wt. % (0.88 g of 45 wt. %) of dispersion was mixed in 40 mL of aqueous 0.1 M NaCl solution. The diluted latex was stirred mechanically for 15 seconds at room temperature, before being titrated against a standardized NaOH (1.0 M) solution.

Zeta Potential Measurement

Zeta potential measurements were measured, using a Malvern Zetasizer NanoZS90 (Malvern Instruments Ltd.) instrument. A latex concentration of 0.01 wt. % was prepared that contained NaNO3 (0.001 wt. %). The dilute mixture was transferred to the measurement cell using a 1 mL plastic syringe. The software-derived average zeta potential and the electrophoretic mobility was then averaged from three measurements. The measurement temperature was set at 25° C.

Determination of Dynamic Mechanical Properties

A TA-Q800 Instrument dynamic mechanical thermal analyzer in tension mode was used to measure viscoelastic behavior of the materials studied. The film specimens were in the form of rectangular strips that had dimensions of 15 mm×5.5 mm×0.5 mm. Measurements were conducted at temperature −110° C. to 200° C. at a heating rate of 3° C. min-1 and frequency of 1 Hz. The obtained data measured the storage modulus (E'), loss modulus (E") and tan δ values (E"/E') as a function of temperature from −110 to 200° C.

Determination of Tensile Properties:

A Hounsfield H10KS tensile instrument (2000 N load-cell) equipped with a laser extensometer was used to measure the tensile properties of the specimens. Films were cut into dumbbell-shapes using a steel die that possessed a length of 75.0 mm and a width of 4.0 mm at its narrowest part, extended over a length of 25 mm. The films were conditioned in a climate-controlled room at 25° C. (±2) at 50% (±5) relative humidity for 24 hours before measuring. The extension rate was determined at a constant crosshead speed of 500 mm per minute.

The measurement was carried out at 25° C. and 50% RH. The reported results are the values averaged from 3-5 measurements.

Polymerization Equipment

A 2 L volume five-necked reaction glass vessel was immersed in a water bath equipped with a temperature controller; the reactor lid had suitable entry points for a mechanical stirrer, a condenser for the cooling system, argon gas and a reactant feeding inlet. The stirrer rate indicator was kept constant at 250 rpm. The temperature of the polymerization was maintained at 75° C. The reactants for emulsion polymerization were fed at a rate of −5.50 g min-1 (for core growth) and −3.21 g min-1 (for shell-growth stage) using a Watson-Marlow Model 505S peristaltic pump.

BA=n-butyl acrylate
ACN=acrylonitrile
BDDA=1,4-butanediol diacrylate
MAA=methacrylic acid
t-ddm=tertiary dodecyl mercaptan
GMA=glycidyl methacrylate
KPS=Potassium persulfate
TSC=total solid content
PS=particle size
DLS=Dynamic light scattering
TEM=Transmission Electron Microscope
DMTA=Dynamic Mechanical Thermal Analysis In the following, the use of the word "latex" is interchangeable with "dispersion", "emulsion" or "heterogenous".

In the following all part and percentages are based on weight unless otherwise specified.

Example 1: Preparation of Seed Latex

In the equipment detailed above, deionized water (300 g) was added to the reaction vessel and purged for 20 min with argon. To this was then added an aqueous solution of the surfactant Aerosol MA-80®, Sodium dihexyl sulfosuccinate, supplied by Solvay (Aerosol MA-80®, used as supplied 14 g dissolved in 76 g of deionized water). After 5 minutes of agitation under a stream of argon and with constant stirring at 250 rpm, butyl acrylate monomer (54.0 g, 0.42 mol) was added and stirred for 5 minutes. Finally, the initiator solution comprising potassium persulfate (1.37 g dissolved in 54 g of deionized water) was added (time=0). After polymerizing for 60 minutes at 75° C., the seed particles were obtained with an average particle size of 45 nm (by DLS) and 43 (15) nm (by TEM).

It was found that it is important to control the targeted particle size of seed to −50 nm in order to obtain the formation of monodisperse final core-shell particles of −100 nm diameter. The results for the seed particles are given in Table 1.

Example 2: Preparation of the Core Latex

The core nanoparticles were prepared using the seed latex of Example 1. Immediately upon completion of the seed stage, a mixture of a pre-emulsion of surfactant (Aerosol MA-80), butyl acrylate, tertiary-dodecyl mercaptan and potassium persulfate in deionized water was continuously added using a metering pump with a feed rate of 5.50 g min$^{-1}$. The polymerization was continued for 135 minutes after completion of the addition of the pre-emulsion to the reaction vessel in order to obtain the core latex.

The pre-emulsion comprised the following, deionized water (171.45 g), tertiary-dodecyl mercaptan (0.085 g), Aerosol MA-80 (2.97 g) and butyl acrylate (237.50 g, 2.13 mol) which were mixed and stirred for 30 minutes prior to commencement of the delayed addition.

The obtained core particles had an average particle size of 79 nm (by DLS) and 80 (28) nm (by TEM). The results for the core particles are given in Table 1.

Example 3: Preparation of Core-Shell Particles Comprising a Crosslinked Shell

To a repeat latex of Example 2, was added a pre-emulsion comprising Aerosol MA-80 (2.97 g), tertiary-Dodecyl mercaptan (0.085 g) and the shell co-monomer solution (237.51 g, comprising butyl acrylate (64 wt. %, 152.00 g), acrylonitrile (30 wt. %, 71.25 g), methacrylic acid (5 wt. %, 11.88 g) and 1,4-butanediol diacrylate (1 wt. %, 2.38 g)) using a metering pump set at a feed rate of 3.21 g min$^{-1}$. After the reaction was completed (4 hours in total at 75° C.), the latex was cooled immediately in an ice container. It was then filtered through a sieve (28 μm) to separate any coagulum. The obtained core-shell particles had an average particle size of 76 nm (by DLS) and 63 (16) nm (by TEM). The results for the core-shell particles are given in Table 1.

Example 4: (Comparative) Preparation of Core-Shell Particles without Crosslinking of the Shell To the latex of Example 2, was added a pre-emulsion comprising Aerosol MA-80 (2.97 g), tertiary-Dodecyl mercaptan (0.085 g) and the shell co-monomer solution (237.51 g, comprising butyl acrylate (65 wt. %, 154.38 g), acrylonitrile (30 wt. %, 71.25 g) and methacrylic acid (5 wt. %, 11.88 g) using a metering pump with feed rate of 3.21 g min$^{-1}$. After the reaction was completed (4 hours in total at 75° C.) the latex was cooled immediately in an ice container. It was filtered through a sieve (28 μm) to separate any coagulum. The obtained core-shell particles had an average particle size of 97 nm (by DLS) and 93 (20) nm (by TEM). The results for the core-shell particles are given in Table 1.

Example 5: Preparation of Core-Shell Particles Comprising a Crosslinked Shell

To a repeat latex of Example 2, was added a pre-emulsion comprising Aerosol MA-80 (2.97 g), tertiary-Dodecyl mercaptan (0.085 g) and the shell co-monomer solution (237.51 g, comprising butyl acrylate (64 wt. %, 154.38 g), acrylonitrile (30 wt. %, 71.25 g) and methacrylic acid (5 wt. %, 11.88 g) and 1,4-butanediol diacrylate (1 wt. %, 2.38 g) using a metering pump with feed rate of 3.21 g min$^{-1}$. After the reaction was completed (4 hours in total at 75° C.) the latex was cooled immediately in an ice container. It was filtered through a sieve (28 μm) to separate any coagulum. The obtained core-shell particles had an average particle size of 95 nm (by DLS) and 91 (15) nm (by TEM). The results for the core-shell particles are given in Table 1.

Example 6: Preparation of Core-Shell Particles Comprising a Crosslinked Shell

To a repeat latex of Example 2, was added a pre-emulsion comprising Aerosol MA-80 (2.97 g), tertiary-Dodecyl mercaptan (0.085 g) and the shell co-monomer solution (237.51 g, comprising butyl acrylate (66 wt. %, 156.75 g), acrylonitrile (28 wt. %, 66.5 g) and methacrylic acid (5 wt. %, 11.88 g) and 1,4-butanediol diacrylate (1 wt. %, 2.38 g) using a metering pump with feed rate of 3.21 g min$^{-1}$. After the reaction was completed (4 hours in total at 75° C.) the latex was cooled immediately in an ice container. It was filtered through a sieve (28 μm) to separate any coagulum. The obtained core-shell particles had an average particle size of 96 nm (by DLS) and 84 (14) nm (by TEM). The results for the core-shell particles are given in Table 1.

Example 7: Preparation of core-shell particles comprising a crosslinked shell

To a repeat latex of Example 2, was added a pre-emulsion comprising Aerosol MA-80 (2.97 g), tertiary-Dodecyl mercaptan (0.085 g) and the shell co-monomer solution (237.51 g, comprising butyl acrylate (71 wt. %, 168.63 g), acrylonitrile (23 wt. %, 54.63 g) and methacrylic acid (5 wt. %, 11.88 g) and 1,4-butanediol diacrylate (1 wt. %, 2.38 g) using a metering pump with feed rate of 3.21 g min$^{-1}$. After the reaction was completed (4 hours in total at 75° C.) the latex was cooled immediately in an ice container. It was filtered through a sieve (28 μm) to separate any coagulum. The obtained core-shell particles had an average particle size of 93 nm (by DLS) and 82 (24) nm (by TEM). The results for the core-shell particles are given in Table 1.

Example 8: Preparation of Core-Shell Particles Comprising a Crosslinked Shell

To a repeat latex of Example 2, was added a pre-emulsion comprising Aerosol MA-80 (2.97 g), tertiary-Dodecyl mercaptan (0.085 g) and the shell co-monomer solution (237.51 g, comprising butyl acrylate (74 wt. %, 175.75 g), acrylonitrile (20 wt. %, 44.5 g) and methacrylic acid (5 wt. %, 11.88 g) and 1,4-butanediol diacrylate (1 wt. %, 2.38 g) using a metering pump with feed rate of 3.21 g min$^{-1}$. The latex was then maintained at 75° C. for a further 55 minutes to complete the polymerization. After the reaction was completed the latex was cooled immediately in an ice container, it was then filtered through a sieve (28 μm) to separate any coagulum. The obtained core-shell particles had an average particle size of 90 nm (by DLS) and 83 (20) nm (by TEM). The results for the core-shell particles are given in Table 1.

TABLE 1

| | Latex properties | | | |
|---|---|---|---|---|
| Example | φc (nom)$^a$ | $d_z^b$ (nm) | $d_{TEM}^c$ (nm) | $\delta_{DLS}^d$ (nm) |
| 1 | 1.00 | 45 | 43 (15) | NA |
| 2 | 1.00 | 79 | 80 (28) | NA |
| 3 | 0.19 | 76 | 63 (16) | 15.5 |
| 4 | 0.55 | 97 | 93 (20) | 9.0 |
| 5 | 0.55 | 95 | 91 (15) | 8.0 |
| 6 | 0.55 | 96 | 84 (14) | 8.5 |
| 7 | 0.55 | 93 | 82 (24) | 7.0 |
| 8 | 0.55 | 90 | 83 (20) | 6.0 |

$^a$= nominal volume fractions of core present based on 100% conversion.
$^b$= z-average diameter measured using DLS at pH 5.0.
$^c$= number-average diameter of particle measured using TEM (The number in parenthesis is the coefficient of variation).
$^d$= Shell thicknesses, calculated from DLS data using: $(dz_{(cs)} - dz_{(c)})/2$, where $dz_{(cs)}$ and $dz_{(c)}$ are the z-average diameters for the final core-shell and core nanoparticles, respectively.
NA = not applicable Example 9: pH Response of the Examples, and the Influence of Crosslinking the Shell, of the Core-Shell Polymer Particles During the preparation of coated and dipped films prepared from the polymers of this invention, it may be necessary to increase the pH of the latex to enhance storage stability, or to compound-in an metal, preferably a multivalent metal, for example zinc ions (in the form of zinc oxide) to form ionomeric crosslinks to form a self-supported nitrile latex film is known in the state of the art, see for example see "Crosslinking in carboxylated nitrile rubber dipped films", Kells, A. and Groves, B. (paper presented at Latex 2006: Frankfurt, Germany, 24-25 Jan. 2006). Furthermore, the viscosity—pH response of the latex is critical to the quality of the cast or dipped film form such carboxylated latexes. The $d_z$ values for the nanoparticles were measured by dynamic light scattering, as a function of pH, and the results are shown in FIG. 1:

FIG. 1 demonstrates that the presence of a crosslinked shell negated any pH response of the latex, and visual reference showed that whilst all of the Examples were free flowing liquids at pH 3, Example 4 formed a gel at pH 8, whilst as an example, Example 5 remained as a free-flowing latex.

Example 10: Estimation of the Available Methacrylic Acid by Potentiometric Titration The measured methacrylic acid (MAA) (wt. %) values were determined from titration data by applying the following equation:

MAA (wt. %)=(($V_{KOH} \times C_{KOH}$)/($m_{dispersion} \times$TSC (wt. %)$_{dispersion}$)$\times$Mw$_{(MAA)}$   (3)

MAA (wt. %)=(Mass of MAA neutralized)/mass of solid polymer)×100   (4)

whereby $V_{KOH}$ and $C_{KOH}$ are the volume of KOH at the neutralization point (from point of maximum gradient of the plot of Ph versus KOH added) and concentration of the KOH solution, respectively. $M_{dispersion}$ is the mass of polymer dispersion used for the titration (the weight solid percentage of polymer dispersion used. Mw (MAA) is the molecular weight of MAA which is 86.09 g mol−1.

TABLE 2

Potentiometric titration data

| Example | MAA[a] (wt. %) | MAA[b] (wt. %) |
|---|---|---|
| 3 | 4.0 | 3.8 |
| 4 | 2.3 | 2.9 |
| 5 | 2.3 | 2.1 |
| 6 | 2.3 | 2.6 |
| 7 | 2.3 | 2.3 |
| 8 | 2.3 | 2.5 |

[a] = nominal concentration of MAA in the whole particle based on composition,
[b] = measured MAA concentration value calculated from titration data.

Equipment for Functionalizing the Shell of the Core-Shell Latex

One third of a 1 L round-bottom conical glass vessel was placed in a paraffin oil bath at 40° C. The reaction mixture was magnetically stirred, the rate of agitation was controlled by setting the magnetic stirrer plate at a constant speed of 250 rpm. The nanoparticle dispersions were functionalized with glycidyl methacrylate; the amount of glycidyl methacrylate (g) added to the latex to be functionalized is shown in Table 3.

An acid-base potentiometric titration was used to detect the degree of glycidyl methacrylate functionalization that had been achieved, through the reduction in the detectable methacrylic acid, wt. % in the resultant functionalized core-shell latex. That is, it detected the quantity of methacrylic acid which had not undergone the esterification reaction with the glycidyl methacrylate functionalization. Titration data (Table 3) shows the reduction for the methacrylic acid contents that were obtained.

Example 11: Functionalization of Example 3

Example 3 (300 g, 10 wt. %) was adjusted to pH 5.0 using 0.5 M aqueous KOH solution. The mixture was stirred initially at 250 rpm for 15 min before it was added to a 1 L flask. Then an aliquot of glycidyl methacrylate (5.94 g, 4.18 mole %) was added to the flask and the mixture was heated at 40° C. at 250 rpm for 8 hours. Unreacted glycidyl methacrylate was removed using a separating funnel. The nanoparticle dispersion was washed two times with 200 ml chloroform. The residual chloroform in the glycidyl methacrylate-functionalised latex was removed by evaporation using a rotary evaporator at a temperature of 25° C. The thus purified latex was then concentrated to 12 wt. % using the rotary evaporator. The characterisation data obtained for the functionalised core-shell Example 9 is given in Table 3, where it is compared to the unfunctionalized core-shell precursor latex, Example 3. It can be seen that there has been a reduction in the wt. % methacrylic acid detected following the functionalization, from 3.8 wt. % to 1.7 wt. % respectively. This difference is then used to calculate the mole % glycidyl methacrylate now present on the latex particles following the reaction between the carboxylic acid groups on the latex particle and the oxirane group on the glycidyl methacrylate, in the case of Example 9, this is 2.5 mole %.

Example 12: Functionalisation of Example 5

Example 5 (300 g, 10 wt. %) was adjusted to pH 5.0 using 0.5 M aqueous KOH solution. The mixture was stirred initially at 250 rpm for 15 min before it was added to a 1 L flask. Then an aliquot of glycidyl methacrylate (53.42 g, 2.41 mole %) was added to the flask and the mixture was heated at 40° C. at 250 rpm for 8 hours. Unreacted glycidyl methacrylate was removed using a separating funnel. The nanoparticle dispersion was washed two times with 200 ml chloroform. The thus purified latex was then concentrated to 12 wt. % using the rotary evaporator. The residual chloroform in the glycidyl methacrylate-functionalised latex was removed by evaporation using a rotary evaporator at a temperature of 25° C. The characterisation data obtained for Example 10 before (i.e. Example 5) and after functionalization with glycidyl methacrylate is given in Table 3. The mole % glycidyl methacrylate now present on the latex particles is 1.5 mole %.

Example 13

This is a repeat of Example 12, except that the latex of Example 8 replaces the latex of Example 5.

TABLE 3

Titration data for nanoparticles before and after functionalization

| Example | pH[a] | MAA[b] (wt. %) | Example | pH[a] | MAA[b] (wt. %) | GMA[c] (mol %) |
|---|---|---|---|---|---|---|
| 3 | 3.4 | 3.8 | 11 | 5.2 | 1.7 | 2.5 |
| 5 | 3.0 | 2.7 | 12 | 5.1 | 2.0 | 1.5 |
| 8 | 3.1 | 2.7 | 13 | 5.0 | 1.9 | 2.0 |

[a] = pH of final dispersion.
[b] = MAA content based on potentiometric titration data.
[c] = GMA added to the latex particles (mole %).

The stability of the thus functionalized latex particles was then evaluated by measuring the z-average diameter ($d_z$), zeta potential ($\xi$) and number-average diameter from TEM ($d_{TEM}$). Without wishing to be bound by theory, it is believed that constancy of these parameters are important to enable the preparation of analogous films. Table 4 shows the characterization data for the latex particles before and after functionalization with glycidyl methacrylate, respectively.

TABLE 4

Latex characterization data before, and after functionalization

| | Before | | | | After | | | |
|---|---|---|---|---|---|---|---|---|
| Example | $d_z$[a] (nm) | $d_{TEM}$[b] (nm) | $\xi$[c] (mV) | Example | $d_z$[a] (nm) | $d_{TEM}$[b] (nm) | $PDI_{DLS}$[d] | $\xi$[d] (mV) |
| 3 | 76 | 63 (16) | −46 | 11 | 81 | 72 (16) | 0.091 | −41 |
| 5 | 95 | 91 (15) | −53 | 12 | 108 | 103 (15) | 0.048 | −50 |
| 8 | 90 | 83 (20) | −49 | 13 | 96 | 83 (12) | 0.067 | −68 |

[a] = values determined from DLS.
[b] = number-average diameter (at least 100 particles) measured by TEM (The numbers in brackets are the coefficient of variation).
[c] = zeta potential values measured at pH 5.0. The sample concentration 0.01 wt. % with a presence of 0.001M sodium nitrate, NaNO₃
[d] = Values determined from DLS.
[e] = Zeta potential values measured at pH 6.0. The sample concentration 0.01 wt. % with a presence of 0.001M sodium nitrate, NaNO₃

Table 4 shows that both $d_z$ and $d_{TEM}$ were only minimally increased after functionalization, without wishing to bound by theory this is believed to reflect the functionalization of the surface carboxylic acid groups. Low polydispersity values were observed for all of the functionalized-dispersions, and the zeta potential values were not significantly different before, and after functionalization.

ramp of −110° C. to 200° C. at a heating rate of 3° C. min$^{-1}$ and frequency of 1 Hz. The obtained data measured the storage modulus (E'), loss modulus (E") and tan δ values (=E"/E') as a function of temperature.

The Tg values obtained for the core-shell polymers are given in Table 5.

TABLE 5

Characterization data for the latex films

| Example | pH$^a$ | $T_A{}^b$ (° C.) | $Tg_{(c)}{}^c$ (° C.) | $Tg_{(s)}{}^c$ (° C.) | $E^d$ (MPa) | $\sigma_b{}^e$ | $\epsilon_b{}^f$ |
|---|---|---|---|---|---|---|---|
| 2  | 8 | 25 | −39 | ND | 0.19 ± 0.05 | 0.10 ± 0.004 | 179 ± 16 |
| 3  | 5 | 25 | −36 | 39 | 66.0 ± 31.4 | 13.1 ± 0.37 | 240 ± 22 |
| 3  | 8 | 25 | −44 | 33 | 23.1 ± 2.50 | 7.41 ± 0.25 | 241 ± 14 |
| 3  | 5 | 90 | NM  | NM | 107 ± 33.1 | 16.1 ± 1.06 | 244 ± 10 |
| 11 | 5 | 25 | −42 | 33 | 12.8 ± 1.79 | 5.23 ± 0.68 | 251 ± 21 |
| 11 | 5 | 90 | −38 | 36 | 109.0 ± 9.97 | 13.6 ± 1.48 | 212 ± 25 |
| 5  | 8 | 25 | −42 | 40 | 12.7 ± 1.10 | 3.34 ± 0.29 | 202 ± 6 |
| 12 | 5 | 25 | −38 | 42 | 8.08 ± 1.75 | 4.36 ± 0.81 | 271 ± 13 |
| 12 | 5 | 90 | −35 | 46 | 13.3 ± 4.74 | 7.85 ± 0.25 | 238 ± 13 |
| 6  | 8 | 25 | −40 | 40 | 8.38 ± 0.62 | 3.25 ± 0.18 | 237 ± 18 |
| 7  | 8 | 25 | −40 | 27 | 1.40 ± 0.29 | 2.86 ± 0.16 | 434 ± 12 |
| 8  | 5 | 25 | −28 | 25 | 2.88 ± 0.19 | 4.07 ± 0.08 | 414 ± 7 |
| 8  | 8 | 25 | −44 | 24 | 1.04 ± 0.12 | 2.31 ± 0.17 | 445 ± 7 |
| 13 | 5 | 25 | −31 | 24 | 0.63 ± 0.22 | 3.06 ± 0.39 | 370 ± 14 |
| 13 | 5 | 90 | −33 | 27 | 4.36 ± 0.16 | 4.86 ± 1.17 | 301 ± 8 |

$^a$= latex pH at which film was cast
$^b$= annealing temperature of film
$^c$= $Tg_{(c)}$ & $Tg_{(s)}$ are the measured glass transition temperatures of the GMA-functionalized films for the core and shells, respectively, determined from the tan d maxima.
$^d$= Young's modulus
$^e$= Stress at break
$^f$= Strain at break
ND = not detected.
NM = not measured TEM micrographs of core-shell latex samples deposited onto a carbon mesh (note, some deformation may have occurred as the particles dried) and subsequently stained with phosphotungstic acid demonstrate that the functionalization procedure did not appreciably alter the morphology of the latex particles.

Example 14: Preparation of Cast Films, and the Determination of the Glass Transition Temperature(s) Thereof The dispersions (60 g of 12 wt. %) were stirred at 200 rpm for 15 minutes before being poured into the glass mold (100×125 mm) surrounded by a removable stainless steel wall (5 mm high). This mold surface had been previously cleaned and then sprayed with Ambersil Dry PTFE Film Anti-Stick Aerosol spray (supplied by CRC Industries UK Ltd) to prevent the dried film being attached to the mold surface. The mold surface was then allowed to dry to prevent the Ambersil mixing in to the latex. The cast latex film was then placed in a circulating air oven at 25° C. for three days. The film was allowed to dry in a humidity-controlled environment (50% RH) at atmospheric pressure. The dry film typically had an average thickness of 550-600 μm as measured by a set of calipers.

To anneal the films, they were further dried in a circulating air oven at 90° C. for 24 hrs.

Dynamic Mechanical thermal Analysis (DMTA) experiments were carried out on the cast films using a A TA-Q800 Instrument dynamic mechanical thermal analyzer operated in tension mode. The samples were in the form of rectangular strips that had dimensions of 15 mm×5.5 mm×0.5 mm, and the measurements were conducted over a temperature Example 15: Self-Healing Properties of the Films of this Invention Diligent observation noted that when a sample of the cast film was cut in to 2 pieces, it could be re-joined upon holding the interfaces of the two halves together, the self-healing process taking only a few minutes at room temperature.

Figure 2A:
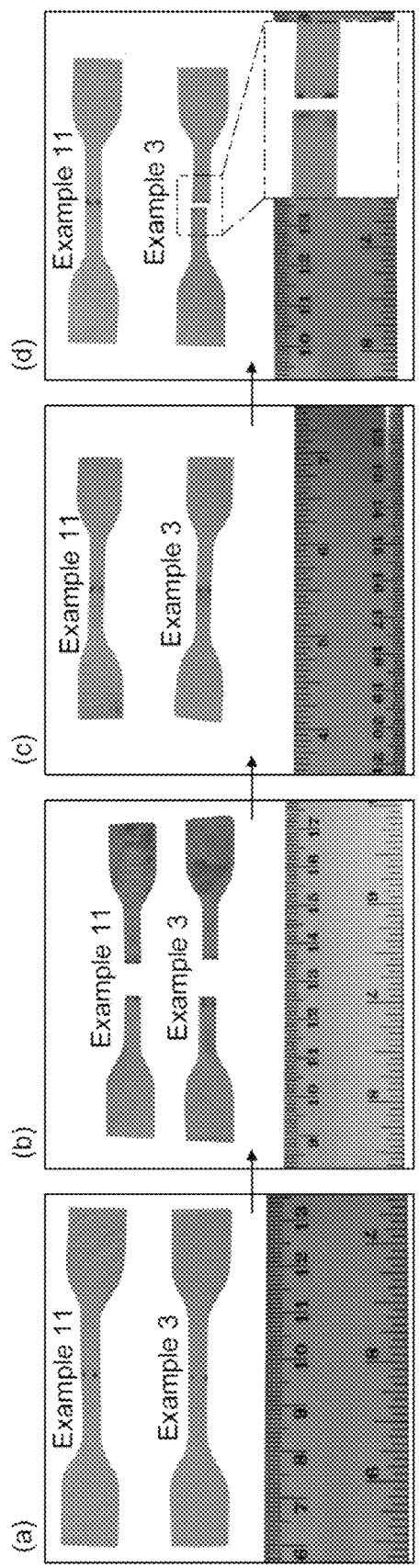
FIG. 2a demonstrates the results obtained when dumbbell films of the non-functionalized Example 3 and the functionalized Example 11 were cut in half using a blade. The stress-strain data shown in FIG. 2b was obtained for examples of dumbbell films which had been cut and rejoined.

In order to improve the self-healing process, and hence to enhance the physical properties of the self-healed films, the cut samples were heated to above the Tg(s) of latex film. FIG. 2a demonstrates the results obtained when dumbbell films of the non-functionalized Example 3 and the functionalized Example 11 were cut in half using a blade, the upper surfaces of the cut dumbbell were immediately marked with 2 dots using a pen, and then rejoined by pressing the two halves together for 60 seconds at room temperature, and then annealing the sample at 40° C. for 24 hours in a circulating air oven.

FIG. 2a shows (a) before cutting, (b) dumbbell cut into 2 pieces and marking the upper surfaces of the dumbbells, (c) Reconnection by pressing for 60 seconds, (d) after annealing at 40° C. for 24 hours. Note, Example 3 (the non-functionalized film) failed after rejoining at room temperature.

Figure 2B:
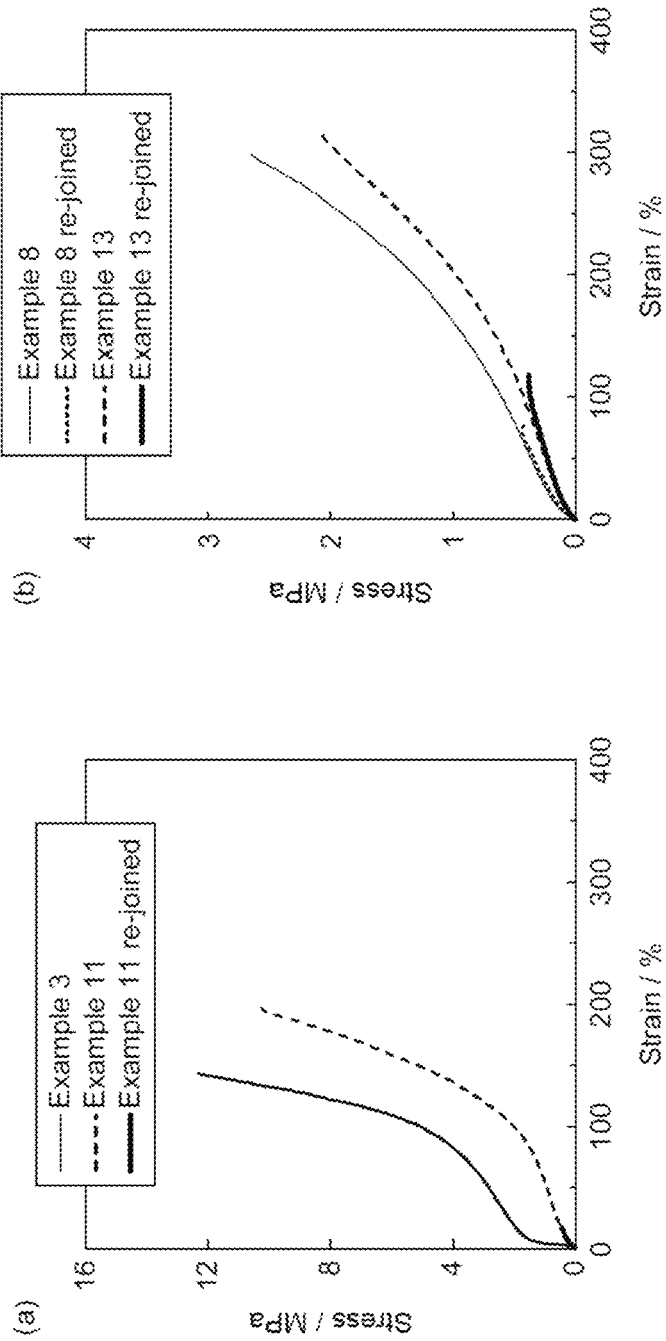

The stress-strain data shown in FIG. 2b was obtained for Examples of dumbbell films which had been cut and rejoined in accordance with the above protocol, using the Hounsfield H10KS (200N load cell):

From the trend in the data, it is postulated that the use of higher annealing temperatures that the 40° C. illustrated here, will further enhance the re-healing processes of the films of this invention. The observation of self-healing properties for these films is expected to enable the healing of pin hole defects in elastomeric film products for example gloves and catheters; or in films which have cavitated, for example the elastomeric films which are used to bind the active ingredients in lithium ion batteries, and which if left un-healed could allow dendrites to form and short-out the battery.

Example 16: Shape-Memory Properties of the Films of this Invention

Diligent observation also discovered that cast films produced from the latexes of this invention were capable of demonstrating shape-memory behavior. In order to further illustrate this observation, strips of film cast from Examples 3 & 11 were immersed in hot (60° C.) water for 30 minutes (i.e. T>$Tg_{(s)}$), removed and immediately wrapped around a cylinder to form a wound spring-like shape before being cooled in cold (15° C.) water (i.e. T<$Tg_{(s)}$), as shown in FIGS. 3(a) & (b). Note, the strip of film cast from Example 11 has been decorated with ink stripes to aid recognition.

Figure 3:
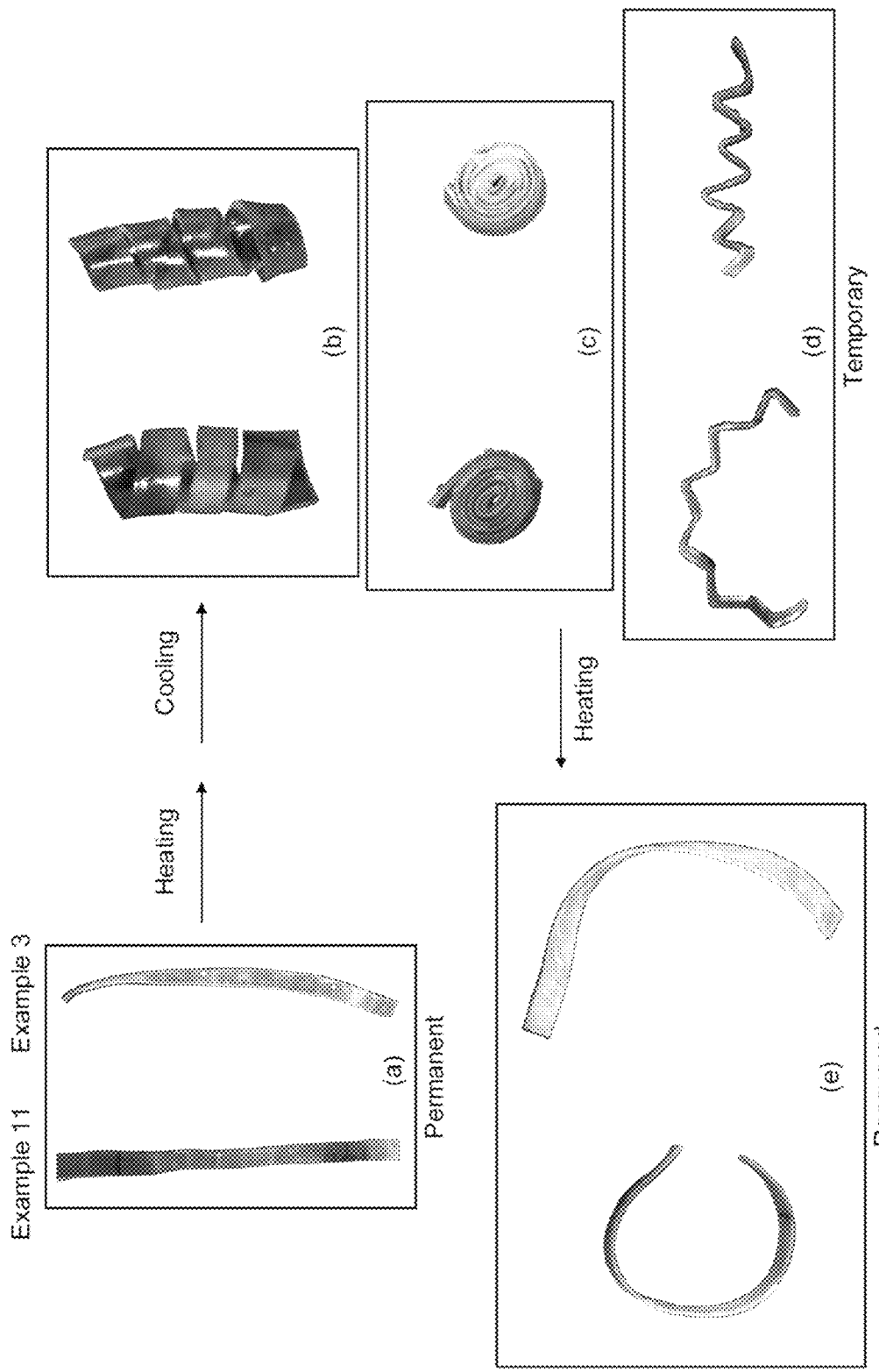
FIGS. 3(a) through 3(e) illustrate the shape-memory properties of strips of film cast from Examples 3 and 11.

The thus shaped samples were then placed into a water bath held at 60° C. for 1 minute, and they were observed to revert back to their near original shape (see FIG. 3 (e)).

The Process was repeated, but this time the samples were wrapped in to a coil shape, before cooling (FIG. 3(c)), and relaxing. A further experiment was conducted in which the relaxed films were placed into a zig-zag configuration using the same protocol (FIG. 3(d)), before relaxing out at 60° C.

Figure 4:
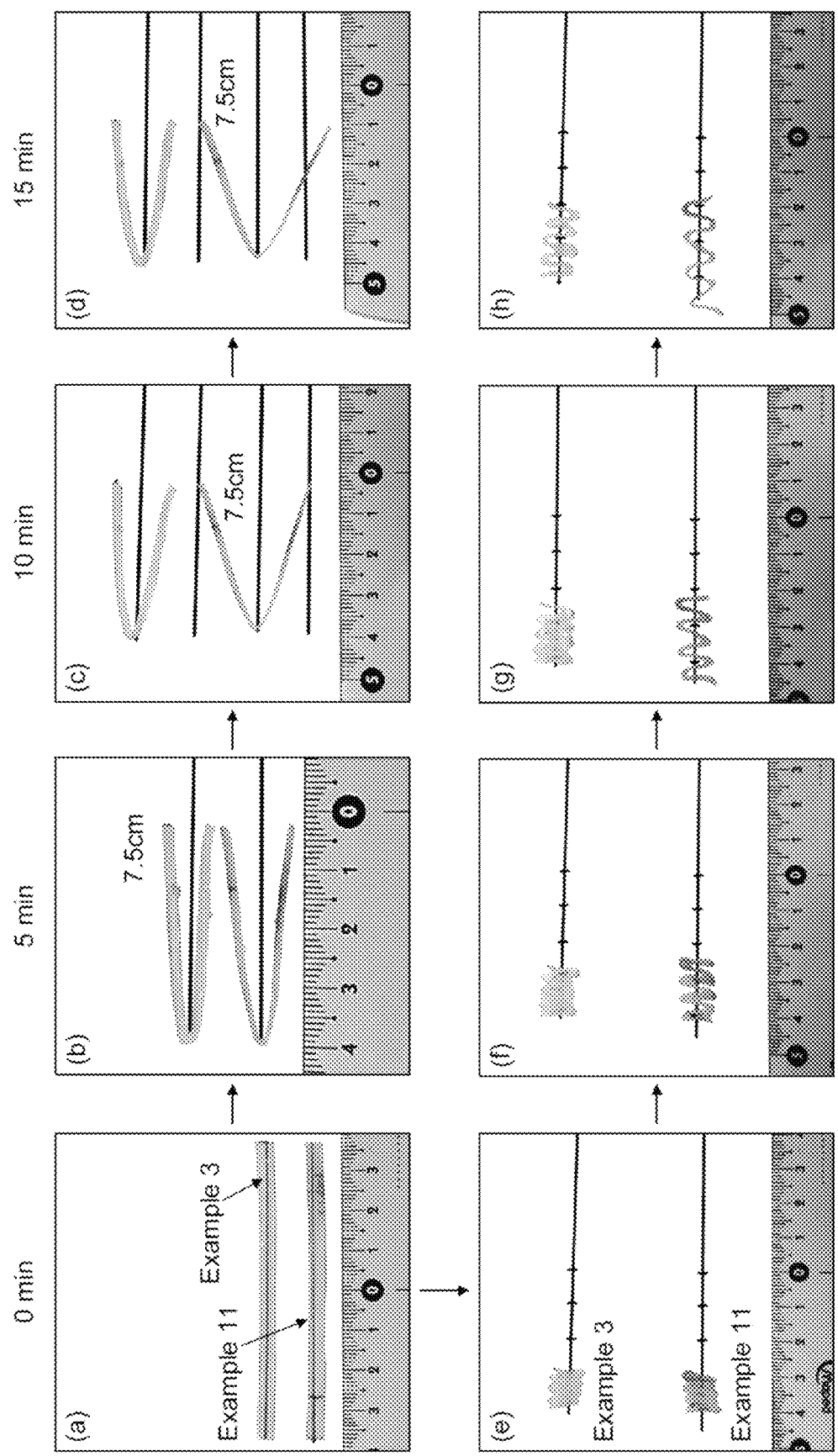
FIGS. 4(a) through 4(h) illustrate the shape-memory relaxation properties of shaped film prepared from Examples 3 and 11.

The shape-memory relaxation of shaped films prepared from Examples 3 and 11 was also evident when stored at room temperature, FIG. 4 illustrates the relaxation of both folded, and spring-like samples prepared according to the temperature profile above, but then allowed to relax at 25° C. as a function of storage time, having been first warmed from storage at 15° C. for 1 minute following the creation of the shape.

The invention claimed is:

1. An aqueous dispersion comprising core-shell polymer latex particles wherein the shell of the core-shell polymer latex particles bears ethylenically unsaturated groups pending from the polymeric backbone of the shell of the latex particles wherein the ethylenic unsaturation is separated from the polymeric backbone by at least 3 chemical bonds and wherein the shell of the core-shell particles is crosslinked and the core of the core-shell particles is not crosslinked.

2. The aqueous dispersion according to claim 1, wherein the shell of the core-shell polymer latex particles comprise structural units represented by formula (1)

$$\text{-L-CR}^1\text{=CR}^2\text{R}^3 \qquad (1)$$

wherein L is a linear or branched divalent group providing at least two atoms in the chain between —$CR^1$=$CR^2R^3$ and the polymeric backbone of the shell of the latex particles or a divalent group comprising a cyclic group and $R^1$, $R^2$, and $R^3$ are independently selected from hydrogen and monovalent organic groups.

3. The aqueous dispersion according to claim 1, wherein -L- is selected from divalent hydrocarbon groups and groups comprising at least one hetero atom in the chain linking —$CR^1$=$CR^2R^3$ to the polymeric backbone.

4. The aqueous dispersion according to claim 1, wherein the core-shell polymer latex particles are made by aqueous emulsion polymerization comprising at least two steps wherein
I) in a step for making the core of the core-shell particles ethylenically unsaturated monomers comprising no monomers containing a plurality of non-conjugated ethylenically unsaturated groups are polymerized; and
II) in a step for making the shell a monomer mixture is polymerized comprising:
a) monomers selected from conjugated dienes, mono ethylenically unsaturated monomers having no functional groups that can be subsequently reacted after formation of the latex particles to introduce ethylenically unsaturated groups and combinations thereof; and
b) i) monomers having at least two non-conjugated ethylenically unsaturated groups that exhibit different reactivities in the aqueous emulsion polymerization, wherein at least a portion of the ethylenically unsaturated groups having the lower reactivity remains unreacted after termination of the aqueous emulsion polymerization; and/or
ii) mono ethylenically unsaturated monomers having functional groups that can be subsequently reacted after formation of the latex particles to introduce ethylenically unsaturated groups; and
c) monomers having at least two non-conjugated ethylenically unsaturated groups different from bi), wherein
if no monomers bi) are present at least a portion of said functional groups of the monomers bii) are reacted after termination of the aqueous emulsion polymerization to introduce ethylenically unsaturated groups.

5. The aqueous dispersion according to claim 4, wherein monomers a) are selected from conjugated dienes, aromatic vinyl compounds, linear alkyl esters of ethylenically unsaturated acids, branched alkyl esters of ethylenically unsaturated acids, linear alkyl amides of ethylenically unsaturated acids, branched alkyl amides of ethylenically unsaturated acids, ethylenically unsaturated nitriles, vinyl esters of carboxylic acids, vinyl ethers, ethylenically unsaturated silanes, alkenes and any combinations thereof; and/or
monomers bi) are selected from allyl (meth)acrylate and allyl crotonate; and/or
monomers bii) are selected from ethylenically unsaturated carboxylic acids, epoxy functional ethylenically unsaturated compounds, hydroxyl functional ethylenically unsaturated compounds, amine functional ethylenically unsaturated compounds and any combinations thereof and/or
monomers c) are selected from monomers comprising two ethylenically unsaturated groups, monomers comprising three ethylenically unsaturated groups, monomers comprising four ethylenically unsaturated groups, and any combinations thereof; and
the monomers for step I) are selected from monomers a) and bii) and combinations thereof.

6. The aqueous dispersion according to claim 5, wherein the conjugated dienes are selected from 1,3-butadiene, isoprene and 2,3-dimethyl-1,3-butadiene; and/or
the aromatic vinyl compounds are selected from styrene, α-methylstyrene, p-methylstyrene, t-butylstyrene and vinyltoluene; and/or
the alkyl esters of ethylenically unsaturated acids are selected from n-alkyl esters, iso-alkyl esters or tert-alkyl esters of (meth)acrylic acid in which the alkyl group has from 1 to 20 carbon atoms, the reaction product of (meth)acrylic acid with glycidyl ester of a neoacid and alkoxyalkyl (meth)acrylate monomers; and/or the amides of ethylenically unsaturated acids are selected from (meth)acrylamide, N-methylol (meth)acrylamide and diacetone acrylamide; and/or the ethylenically unsaturated nitriles are selected from (meth)acrylonitrile and fumaronitrile; and/or the vinyl esters of ethylenically unsaturated acids are selected from vinyl acetate, vinyl proprionate, vinyl butyrate, vinyl benzoate, vinyl-2-ethylhexanoate, vinyl stearate, and the vinyl esters of versatic acid; and/or the ethylenically unsaturated silanes are selected from trimethoxyvinylsilane, triethoxyvinylsilane, trimethylsilyl (meth)acrylate and triethylsilyl (meth)acrylate, 3-(trimethoxysilyl)propyl (meth)acrylate and 3-(trimethoxysilyl)propyl (meth)acrylate; and/or the vinyl ethers are selected from alkyl vinyl ethers; and/or the alkenes are selected from ethene, propene, butene, hexene and cyclohexene; and/or the ethylenically unsaturated carboxylic acids are selected from monofunctional acids and/or difunctional acids; and/or the hydroxyl functional ethylenically unsaturated compounds are selected from hydroxyethyl (meth)acrylate, hydroxypropyl (meth)acrylate and hydroxybutyl (meth)acrylate; and/or the amino functional ethylenically unsaturated compounds are selected from aminoethyl (meth)acrylate, aminopropyl (meth)acrylate and aminobutyl (meth)acrylate; and/or epoxy functional ethylenically unsaturated compounds are selected from glycidyl (meth)acrylate, allyl glycidylether, vinyl glycidylether, vinyl cyclohexene oxide, limonene oxide, 2-ethylglycidylacrylate, 2-ethylglycidylmethacrylate, 2-(n-propyl)glycidylacrylate, 2-(n-propyl)glycidylmethacrylate, 2-(n-butyl)glycidylacrylate, 2-(n-butyl)glycidylmethacrylate, glycidylmethylmethacrylate, glycidylacrylate, (3',4'-epoxyheptyl)-2-ethylacrylate, (3',4'-epoxyheptyl)-2-ethylmethacrylate, (6',7'-epoxyheptyl)acrylate, (6',7'-epoxyheptyl)methacrylate, allyl-3,4-epoxyheptylether, 6,7-epoxyheptylallylether, vinyl-3,4-epoxyheptylether, 3,4-epoxyheptylvinylether, 6,7-epoxyheptylvinylether, o-vinylbenzylglycidylether, m-vinylbenzylglycidylether, p-vinylbenzylglycidylether, 3-vinyl cyclohexene oxide, alpha-methyl glycidyl methacrylate, 3,4-epoxycyclohexylmethyl (meth)acrylate and combinations thereof.

7. The aqueous dispersion according to claim 4, wherein the shell of the core-shell particles is prepared by aqueous emulsion polymerization of a mixture of ethylenically unsaturated monomers comprising group monomers a), monomers bii) and monomers c) and optionally monomers bi) thereby forming polymer latex particles having a shell bearing a first functional originating from the functional group of monomers bii); and subsequently reacting said polymer latex particles bearing said first functional group with an ethylenically unsaturated compound having in addition to the ethylenically unsaturation a second functional group that is reactive with the first functional group.

8. The aqueous dispersion according to claim 7, wherein

A) monomers bii) comprise ethylenically unsaturated carboxylic acids and the first functional group is a carboxyl group and the ethylenically unsaturated compound having the second functional group is selected from epoxy functional ethylenically unsaturated compounds; or B) monomers bii) comprise epoxy functional ethylenically unsaturated compounds and the first functional group is an epoxy group and the ethylenically unsaturated compound having the second functional group is selected from ethylenically unsaturated carboxylic acids; or C) monomers bii) comprise hydroxy and/or amino functional ethylenically unsaturated compounds resulting in first functional groups selected from hydroxy and amino groups and the ethylenically unsaturated compound having the second functional group is selected from isocyanate or thioisocyanate functional ethylenically unsaturated compounds.

9. The aqueous dispersion according to claim 4, wherein the core is built by a seed latex that is pre-made or made in-situ at the beginning of the free radical emulsion polymerization or the core is formed by a seeded free radical emulsion polymerization in presence of a seed latex that is pre-made or made in situ; or the core is formed in a non-seeded free radical emulsion polymerization.

10. The aqueous dispersion according to claim 4, wherein the monomer mixture for polymerizing the core comprises an alkyl ester of (meth)acrylic acid and the monomer mixture for polymerizing the shell comprises:

an alkyl ester of (meth)acrylic acid, an ethylenically unsaturated nitrile compound, an ethylenically unsaturated acid, and a non-conjugated diene; and the core-shell particles are reacted after termination of the aqueous emulsion polymerization with an ethylenically unsaturated epoxy compound.

11. The aqueous dispersion according to claim 1, wherein the core has a lower glass transition temperature $T_g$ than the shell and the $T_g$ of the shell is above 0° C., as measured by Dynamic Mechanical Thermal Analysis at a fixed frequency of 1 Hz, and a heating rate of 3° C. per minute.

12. A method for making an aqueous dispersion comprising core-shell polymer latex particles wherein the shell of the core-shell polymer latex particles bears ethylenically unsaturated groups pending from the polymeric backbone of the shell of the latex particles wherein the shell of the core-shell particles is cross-linked and the core of the core-shell particles is not crosslinked by aqueous emulsion polymerization as defined in claim 4.

13. An elastomeric film made from the aqueous dispersion of claim 1.

14. The elastomeric film according to claim 13, wherein the film is self-supported and substantially free of sulfur cross-links and substantially free of ionomeric cross-links.

15. The elastomeric film according to claim 13 wherein the elastomeric film has a first and second outer surface and an inner core between the first and second outer surface wherein there is a higher degree of crosslinking between polymeric particles at the first and second outer surface then in the inner core of the article.

16. An article comprising the elastomeric film according to claim 13.

17. The article of claim 16 being selected from disposable gloves including surgical gloves, examination gloves, industrial gloves, household gloves, fabric supported gloves, medical devices, condoms and femidoms or the article includes binders for the active ingredients for an energy cell.

18. A method for making a self-supported elastomeric film comprising:

a) providing a composition comprising the aqueous dispersion according to claim 1,
b) applying said composition to a substrate to form a wet film,
c) drying and/or curing the wet film to form an elastomeric film, and
d) separating the elastomeric film from the substrate,
e) optionally heat-treating the elastomeric film prior or after step d) at a temperature from 20° C. to 160° C.

19. The method of claim 18, wherein the providing step a) neither includes the addition of sulfur and accelerators for sulfur vulcanization nor the addition of zinc compounds to the composition.

20. The method of claim 18, wherein the application step b) comprises casting, dip-molding, spraying or knife coating.

\* \* \* \* \*

UNITED STATES PATENT AND TRADEMARK OFFICE
CERTIFICATE OF CORRECTION

| | | |
|---|---|---|
| PATENT NO. | : 12,098,228 B2 | Page 1 of 1 |
| APPLICATION NO. | : 17/423637 | |
| DATED | : September 24, 2024 | |
| INVENTOR(S) | : Peter Shaw, Amir H. Milani and Brian Saunders | |

It is certified that error appears in the above-identified patent and that said Letters Patent is hereby corrected as shown below:

In the Claims

In Claim 6 at Column 31, Line 7, delete "proprionate," and insert -- propionate, --.

In Claim 10 at Column 32, Line 24, delete "to-claim" and insert -- to claim --.

Signed and Sealed this
Twenty-sixth Day of November, 2024

Katherine Kelly Vidal
*Director of the United States Patent and Trademark Office*